(12) United States Patent
Miller et al.

(10) Patent No.: US 12,742,763 B1
(45) Date of Patent: Sep. 22, 2026

(54) SYSTEMS AND METHODS FOR AMBIENT AND INTERNAL MONITORING

(71) Applicant: IDEAL SCIENCES, INC., North Salt Lake, UT (US)

(72) Inventors: Jason Miller, Layton, UT (US); Ian Campbell, Bountiful, UT (US)

(73) Assignee: IDEAL SCIENCES, INC., North Salt Lake, UT (US)

( * ) Notice: Subject to any disclaimer, the term of this patent is extended or adjusted under 35 U.S.C. 154(b) by 0 days.

(21) Appl. No.: 19/295,549

(22) Filed: Aug. 8, 2025

(51) Int. Cl.

| | |
|---|---|
| ***G01D 21/02*** | (2006.01) |
| ***G01J 1/02*** | (2006.01) |
| ***G01K 1/024*** | (2021.01) |
| ***G01K 1/14*** | (2021.01) |
| ***G01N 33/14*** | (2006.01) |

(Continued)

(52) U.S. Cl.
CPC ........... *G01N 33/146* (2013.01); *G01D 21/02* (2013.01); *G01J 1/0233* (2013.01); *G01K 1/024* (2013.01); *G01K 1/14* (2013.01); *G08B 21/185* (2013.01); *G08B 21/20* (2013.01)

(58) Field of Classification Search
CPC .... G01N 33/146; G01N 33/143; G01N 33/14; G01N 33/04; G01N 33/02; G01D 21/02; G01D 21/00; G01J 1/0233; G01K 1/024; G01K 1/14; G01K 1/20; G01K 1/022; G01K 1/026; G01K 1/028; G01K 13/00; G01K 7/42; G01K 7/427; G01K 15/00; G01K 2201/00; G01K 2203/00; G08B 21/185; G08B 21/20; G08B 21/12; G08B 31/00; G08B 25/007; G08B 25/10
USPC ............... 73/49.2, 23.2, 31.05, 31.01, 23.21; 340/584, 506, 539.26, 540, 870.17, 632, 340/602; 374/45; 700/9; 702/130, 188, 702/19, 24, 182, 189, 183, 187, 127, 104, 702/1, 50, 22, 184, 85, 132, 99, 56, 138, 702/54, 31, 81
See application file for complete search history.

(56) References Cited

U.S. PATENT DOCUMENTS 4,935,106 A * 6/1990 Liston ................ G01N 27/3271 205/792
11,022,321 B1 * 6/2021 Bhogal .................... G01K 1/08
11,581,099 B1 * 2/2023 Rufo ...................... G16H 20/13
(Continued)

OTHER PUBLICATIONS

Protmex, Protmex 433 Indoor PTX-2 Remote Senor Weather Station Outdoor Temperature Humidity Wireless Sensor, accessed Mar. 25, 2025, https://www.alibaba.com/product-detail/PROTMEX-433-INDOOR-PTX-2-remote_1600233253531.html.
(Continued)

*Primary Examiner* — Jeffrey P Aiello
(74) *Attorney, Agent, or Firm* — Mertzlufft Law PLLC dba Stake; Joshua Mertzlufft

(57) ABSTRACT

A temperature and humidity monitoring system is disclosed, comprising an ambient sensing device with sensors for temperature, humidity, accelerometer, and light, all connected to a processor and electronic storage unit. The system also includes a networking device for wireless data transmission to a remote device. Additionally, a remote probe may be provided. The remote probe may communicate with the processor to transmit data including ambient and probe temperature, humidity, accelerometer, and light measurements. The processor may store and retrieve data for transmission to the remote device and can send alerts based on predefined event parameters.

21 Claims, 15 Drawing Sheets

(51) Int. Cl.
*G08B 21/18* (2006.01)
*G08B 21/20* (2006.01)

(56) References Cited

U.S. PATENT DOCUMENTS

| | | | | |
|---|---|---|---|---|
| 12,156,536 | B2 | 12/2024 | Fu et al. | |
| 2014/0334516 | A1* | 11/2014 | Verhagen | G01K 1/143 374/44 |
| 2021/0169417 | A1* | 6/2021 | Burton | A61B 5/4857 |
| 2023/0176669 | A1* | 6/2023 | Gupta | G06F 3/0443 345/174 |
| 2023/0403535 | A1* | 12/2023 | Volkerink | G06K 19/07737 |

OTHER PUBLICATIONS

SencKit, 4-Pack WiFi Temperature Humidity Sensor: Wireless Temperature Humidity Monitor with App Alert, Free Data Storage Export, Smart Indoor Thermometer Hygrometer Compatible with Alexa Google Assistant, accessed Mar. 24, 2025, https://www.amazon.com/4-Pack-WiFi-Temperature-Humidity-Sensor/dp/B0B5DQZTG9.

Ideal Sciences, Inc., Temp Stick +Power—Alerts for Temperature, Humidity & Power Outages (archived on the Wayback Machine), Jun. 22, 2024, https://tempstick.com/product/temp-stick-pro-with-buffer-bottle/.

Ideal Sciences, Inc., Temp Stick Pro with Buffer Bottle (archived on the Wayback Machine), Feb. 29, 2024, https://tempstick.com/product/temp-stick-power/.

Ideal Sciences, Inc., Temp Stick® by Ideal Sciences—Official Website (archived on the Wayback Machine), Jul. 24, 2024, https://tempstick.com.

* cited by examiner

SYSTEMS AND METHODS FOR AMBIENT AND INTERNAL MONITORING

BACKGROUND

Monitoring of characteristics of media, for example, temperature and humidity, is an activity finding various applications. One such application is in wine cellars.

Monitoring wine cellars may assist in the preservation and quality of a wine collection. Temperature and humidity are factors that, if not properly controlled, can lead to spoilage. Fluctuations in temperature can cause the wine to expand and contract, potentially damaging the cork and allowing air to enter, which can oxidize the wine. Similarly, improper humidity levels can dry out corks, leading to the same issue. By consistently monitoring these conditions with digital thermometers and hygrometers, and using climate control systems, wine collectors can maintain an optimal environment. This careful attention helps ensure that the wine ages gracefully, retaining its intended flavors and aromas, and ultimately protecting the investment made in the collection.

Temperature in a wine cellar in many cases should be kept between 45° F. and 65° F. (7° C. to 18° C.), with an optimal temperature based on the wines in the collection and the owner's preferences. Often, consistency is important, as fluctuations can cause the wine to expand and contract, potentially damaging the cork and allowing air to seep in. Thermometers and climate control systems can be used to monitor and regulate temperature within the wine cellar.

Humidity levels in a wine cellar should be maintained between 50% and 70%. Proper humidity prevents the corks from drying out and shrinking, which could lead to oxidation and spoilage of the wine. Hygrometers may be used to measure humidity levels, and humidifiers or dehumidifiers can be employed to adjust the environment as needed. In addition to these tools, the cellar's construction materials, such as stone or concrete, can naturally help maintain a stable humidity level. By carefully monitoring and adjusting both temperature and humidity, wine collectors can age their collections gracefully while retaining their intended flavors and aromas.

SUMMARY

This Summary is intended to introduce, in an abbreviated form, various topics to be elaborated upon below in the Detailed Description. This Summary is not intended to identify key or essential aspects of the claimed invention. This Summary is similarly not intended for use as an aid in determining the scope of the claims.

In some aspects, the techniques described herein relate to a ambient sensing device, including: an ambient temperature sensor; an ambient humidity sensor; an accelerometer; a light sensor; a processor in electronic communication with the ambient temperature sensor, the ambient humidity sensor, the accelerometer, and the light sensor; an electronic storage unit including non-volatile memory in electronic communication with the processor; and a networking device in electronic communication with the processor; and a data port in electronic communication with the processor; wherein the processor is configured to: determine whether a remote probe including a remote probe sensor has been installed to the data port; store the data on the electronic storage unit including an ambient temperature measurement measured by the ambient temperature sensor, an ambient humidity measurement measured by the ambient humidity sensor, an accelerometer measurement measured by the accelerometer, and a light measurement measured by the light sensor, and, if a probe sensor has been installed to the data port, a remote probe measurement measured by the remote probe sensor; after the wireless network connection is established, retrieve the data stored on the electronic storage unit and instruct the networking device to transmit the data to the remote device; and instruct the networking device to transmit an alert to the remote device, wherein the alert is sent following a triggering of an event determined by an event parameter.

In some aspects, the techniques described herein relate to an ambient sensing device, wherein the remote probe sensor includes a remote temperature sensor and the remote probe includes fitting configured to secure the remote probe to a container such that the remote temperature sensor is disposed within the container in thermal communication with a fluid disposed within the container.

In some aspects, the techniques described herein relate to a ambient sensing device, including: an ambient temperature sensor; an ambient humidity sensor; a processor in electronic communication with the ambient temperature sensor and the ambient humidity sensor; a networking device in electronic communication with the processor and configured to transmit data to a remote device via a network connection; and a data port in electronic communication with the processor; wherein the processor is configured to: determine whether a remote probe including a remote probe sensor has been installed to the data port; and after the network connection is established, instruct the networking device to transmit the data to the remote device, wherein the data includes one or more of an ambient temperature measurement measured by the ambient temperature sensor, an ambient humidity measurement measured by the ambient humidity sensor, or, if a probe sensor has been installed to the data port, a remote probe measurement measured by the remote probe sensor.

In some aspects, the techniques described herein relate to an ambient sensing device, wherein the processor is configured to instruct the networking device to transmit an alert to the remote device.

In some aspects, the techniques described herein relate to an ambient sensing device, wherein the alert is sent following a triggering of an event determined by an event parameter.

In some aspects, the techniques described herein relate to an ambient sensing device, wherein the remote probe sensor includes a remote temperature sensor and the remote probe includes fitting configured to secure the remote probe to a container such that the remote temperature sensor is disposed within the container in thermal communication with a fluid disposed within the container.

In some aspects, the techniques described herein relate to an ambient sensing device, wherein the data includes an ambient temperature measurement measured by the ambient temperature sensor, an ambient humidity measurement measured by the ambient humidity sensor, and, if a probe sensor has been installed to the data port, a remote probe measurement measured by the remote probe sensor.

In some aspects, the techniques described herein relate to an ambient sensing device, wherein the ambient sensing device includes an electronic storage unit in electronic communication with the processor and the processor is configured to store the data on the electronic storage unit.

In some aspects, the techniques described herein relate to an ambient sensing device, wherein the processor is configured to, after the network connection is established, retrieve the data stored on the electronic storage unit for transmission via the networking device.

In some aspects, the techniques described herein relate to an ambient sensing device, wherein the processor is configured to: receive a transmission schedule from the remote device; store the transmission schedule on the electronic storage unit; and transmit the data via the networking device to the remote device according to the transmission schedule.

In some aspects, the techniques described herein relate to an ambient sensing device, wherein the transmission schedule is a function of an event parameter.

In some aspects, the techniques described herein relate to an ambient sensing device, wherein the data includes an alert.

In some aspects, the techniques described herein relate to an ambient sensing device, wherein the ambient sensing device further includes an accelerometer in electronic communication with the processor and a light sensor in electronic communication with the processor.

In some aspects, the techniques described herein relate to an ambient sensing device, wherein the data includes: the ambient temperature measurement measured by the ambient temperature sensor; the remote probe measurement measured by the remote probe sensor; the ambient humidity measurement measured by the ambient humidity sensor; and a light measurement measured by the light sensor.

In some aspects, the techniques described herein relate to an ambient sensing device, further including an electrical port configured to receive an electrical plug configured for delivery of electrical power from an external electrical power source, wherein the processor is further configured to, in response to a detected loss of electrical power at the electrical port, switch a power supply to the system from the external electrical power source to the internal electrical power source.

In some aspects, the techniques described herein relate to an ambient sensing device, wherein the processor is further configured to, upon switching the power supply to the system, instruct the networking device to transmit a power status alert to the remote device.

In some aspects, the techniques described herein relate to an ambient sensing device, wherein the network connection is a wireless network connection.

In some aspects, the techniques described herein relate to an ambient sensing device, wherein the wireless network connection is a cellular network connection or a local area network connection.

In some aspects, the techniques described herein relate to an ambient sensing device, wherein the processor is configured to select one of a cellular network connection or a local area network connection as the network connection based on one or more of a signal strength comparison or user input.

In some aspects, the techniques described herein relate to an ambient sensing device, wherein the ambient sensing device includes a display in electronic communication with the processor, and the display is configured to display the data.

In some aspects, the techniques described herein relate to a method for monitoring temperature and humidity, including: providing an ambient sensing device, including: an ambient temperature sensor; an ambient humidity sensor; an accelerometer; a light sensor; a processor in electronic communication with the ambient temperature sensor, the ambient humidity sensor, the accelerometer, and the light sensor; an electronic storage unit including non-volatile memory in electronic communication with the processor; and a networking device in electronic communication with the processor; and a data port in electronic communication with the processor; determining, by the processor, whether a remote probe including a remote probe sensor has been installed to the data port; store, by the processor, the data on the electronic storage unit including an ambient temperature measurement measured by the ambient temperature sensor, an ambient humidity measurement measured by the ambient humidity sensor, an accelerometer measurement measured by the accelerometer, and a light measurement measured by the light sensor, and, if a probe sensor has been installed to the data port, a remote probe measurement measured by the remote probe sensor; and after the wireless network connection is established, retrieve, by the processor, the data stored on the electronic storage unit and instruct the networking device to transmit the data to the remote device.

BRIEF DESCRIPTION OF THE FIGURES

For a fuller understanding of the nature and objects of the disclosure, reference should be made to the following detailed description taken in conjunction with the accompanying drawings, in which.

DETAILED DESCRIPTION

Implementations disclosed herein include temperature and humidity monitoring systems for monitoring both characteristics of internal content of a container or another probable object as well as ambient environmental characteristics. Implementations may monitor the internal and ambient characteristics for storage on a local device, as well as transmission over a network to a remote device.

Implementations disclosed herein solve the problem of the difficulty of remotely monitoring characteristics of contents of a container (e.g., a wine bottle, buffer bottle, canister, etc.) or another probable object (e.g., food, cooler, pipe with a pipe clamp probe, etc.) simultaneously with ambient characteristics where a remote device is dynamically located and/or connected relative to the monitoring device. This problem exists because in practical usage, a user's remote device (e.g., a smartphone) is typically not stationary for the duration of time during which monitoring of characteristics is desirable.

Physical movement of the user's remote device causes difficulties in maintaining a singular connection (e.g., networked, wired, wireless, or peripheral) with a sensing device. In instances implementing a wired connection (e.g., network or peripheral), physical movement of the user's remote device may be limited to the range of the wiring used for the connection. In instances implementing a wireless network connection, physical movement may cause loss or change of connection between the remote device and the sensing device.

Further, a network connection between the user's remote device may not be consistent—it may be unstable or selectively enabled. In such embodiments, temperature logging onboard the remote device itself may be unreliable or inconsistent.

Implementations disclosed herein solve all or some of these shortcomings.

Implementations herein include systems for monitoring temperature and humidity and methods of using the same. The system may include an ambient sensing device and a remote probe. The ambient sensing device may include an ambient temperature sensor, an ambient humidity sensor, a connection to the remote probe, a processor in electronic communication with the ambient temperature sensor and the ambient humidity sensor, and a networking device in electronic communication with the processor, the networking device configured to transmit data to a remote device via a network connection. The processor may be further configured to instruct the networking device to transmit an alert to the remote device. The alert may be sent following a triggering of an event determined by an event parameter.

Figure 1:
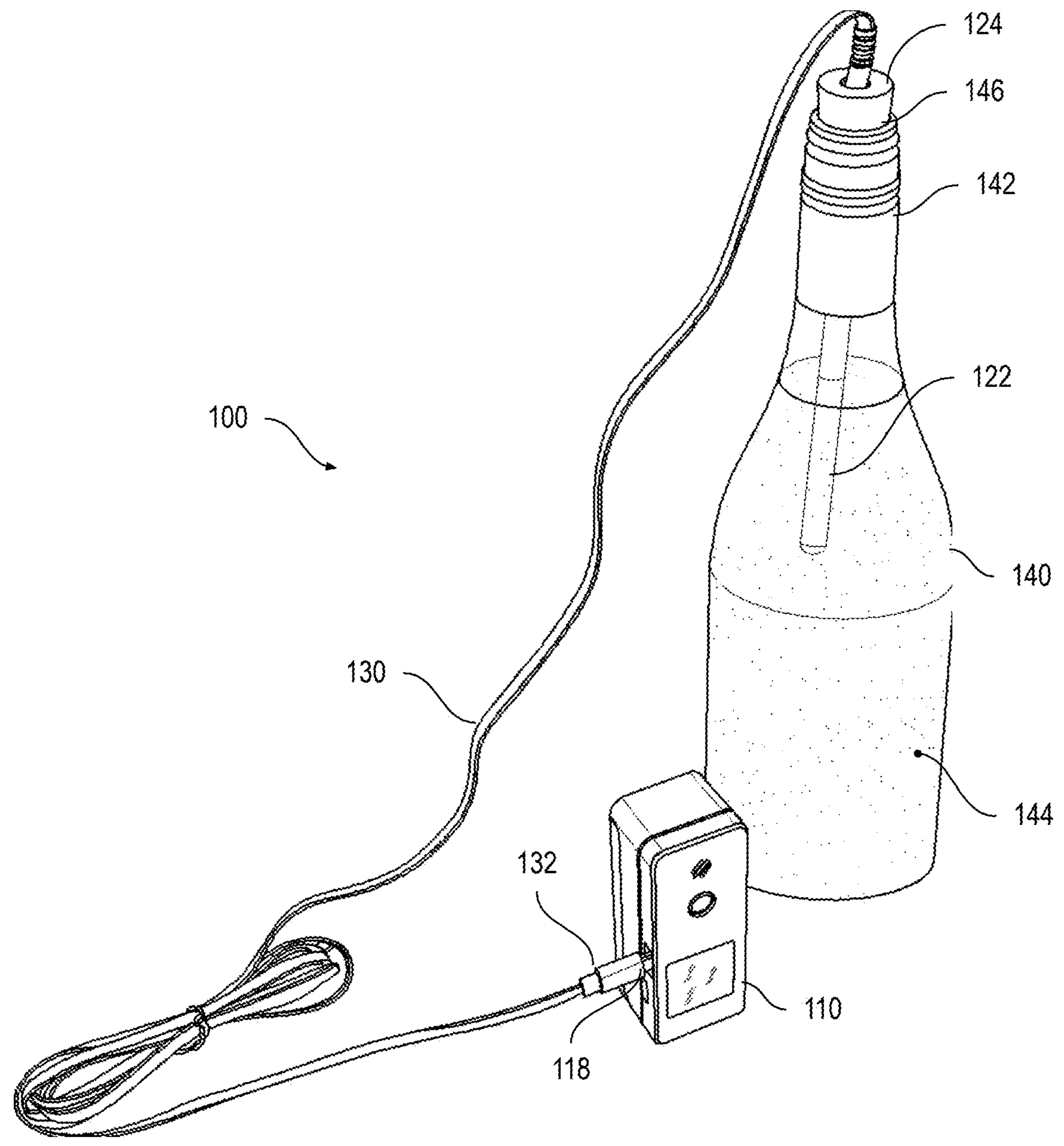
FIG. 1 illustrates an example implementation of a system for simultaneous monitoring of internal and ambient characteristics, according to one or more implementations herein.

FIG. 1 illustrates an example implementation of a system 100 for simultaneous monitoring of internal and ambient characteristics, according to one or more implementations herein. The system 100 is configured to measure internal characteristics of a wine bottle 140. An ambient sensing device 110 and a remote probe 122 of the system 100 may enable remote monitoring of the contents of the wine bottle 140 and the ambient environment even if there is a loss of connectivity between the ambient sensing device 110 and a user's remote device.

The system 100 includes a wine bottle 140, which may contain a quantity of wine 144 therein. While the wine bottle 140 is depicted as standing upright, it will be understood that the wine bottle 140 may be disposed in a variety of orientations, such as, for example, laying on its side (e.g., on a wine rack within a wine cellar). The wine bottle 140 may be located, for example, in a wine cellar. The wine bottle 140 may narrow in its radius at a shoulder along a neck 142 toward an opening 146 in the wine bottle.

The wine bottle 140 may have therein disposed the remote probe 122. The remote probe 122 may include a fitting 124 configured for fitment into the neck 142 via the opening 146. The remote probe 122 may include, for example, a temperature sensor (e.g., a thermocouple or a thermistor) disposed therewithin such that the temperature sensor may substantially or fully equilibrize in temperature with the wine 144 within the wine bottle 140.

Leading from the remote probe 122 may be a cable 130 configured for transmission of electrical signals to the ambient sensing device 110. The cable 130 may, distal to its end proximate the fitting 124, conclude with a plug 132 (e.g., a peripheral connector such as a USB or serial connector). The plug 132 may correspond with and be connectable to a data port 118 of the ambient sensing device 110.

In some implementations, the remote probe 122 may include disposed therein an electronic circuit configured to convert an analog signal received from the temperature sensor to a digital signal for transmission. In such implementations, the electronic circuit may be powered by a power circuit within the cable 130 and powered by the ambient sensing device 110.

The ambient sensing device 110 may receive temperature readings in the form of electronic signals from the remote probe 122. In some implementations, the ambient sensing device 110 may measure properties of the environment in which it is located (e.g., a wine cellar) such as, for example, temperature, humidity, light, and accelerations using hardware such as a temperature sensor, barometer, light sensor, and accelerometer, respectively. The ambient sensing device 110 may include onboard electronics to record measurements both from its internal sensors and from the remote probe 122. Such onboard electronics may further include a communications module configured to transmit recorded measurements from the ambient sensing device 110 to a remote device of a user (e.g., a smartphone). Such a transmission may in some implementations be direct from the ambient sensing device 110 to the remote device (e.g., via a direct wireless or wired connection between the ambient sensing device 110 and the remote device) or in other implementations may be via a network (e.g., via a direct wireless or wired connection to a local area network (LAN), a cellular network, and/or the Internet). The data may be computed by the processor to yield a heat index or dew point, which may be transmitted also.

The ambient sensing device 110 may also compute a heat index based on the ambient temperature and ambient humidity measurements. The heat index, an apparent temperature, quantifies how hot it feels when relative humidity is combined with the air temperature. Its calculation often involves complex empirical formulas that use a regression equation or lookup tables. These formulas typically take into account the non-linear interaction between temperature and humidity, as higher humidity reduces the body's ability to cool itself through evaporation, leading to a perceived increase in temperature. The computed heat index can then be transmitted to a remote device alongside the raw temperature and humidity data.

The ambient sensing device 110 may also compute a dew point based on the ambient temperature and ambient humidity measurements. The dew point, the temperature at which air becomes saturated with water vapor and dew begins to form, can be calculated using various psychrometric formulas. These calculations typically involve converting relative humidity and temperature into actual vapor pressure, then using that vapor pressure to determine the temperature at which saturation would occur. The computed dew point can then be transmitted to a remote device alongside the raw temperature and humidity data.

The ambient sensing device 110 may be configurable to receive a transmission schedule, such as a transmission periodicity or an alert threshold, for any given property it is configured to measure. Thus, the ambient sensing device 110 may transmit recorded measurements and/or alerts according to the transmission schedule.

The ambient sensing device 110 may store a history of data in an onboard memory. For example, in the event of an expected or unexpected interruption in the connection between the ambient sensing device 110 and the remote device, when the ambient sensing device 110 determines the connection is restored, the ambient sensing device 110 may then transmit the data stored thereon to the remote device.

In some implementations, the ambient sensing device 110 may include a display and a button. The display may present for visual inspection condition readings (e.g., temperature readings, humidity readings, battery level readings, connection strength readings, and alert readings), settings, and more. The button may be configured for control and local operation of the ambient sensing device 110.

As such, the ambient sensing device 110 and the remote probe 122 may enable remote monitoring both of temperature of the wine 144 within the wine bottle 140 and the ambient properties of the environment (e.g., the wine cellar) in which the ambient sensing device 110 is located.

Figure 2A:
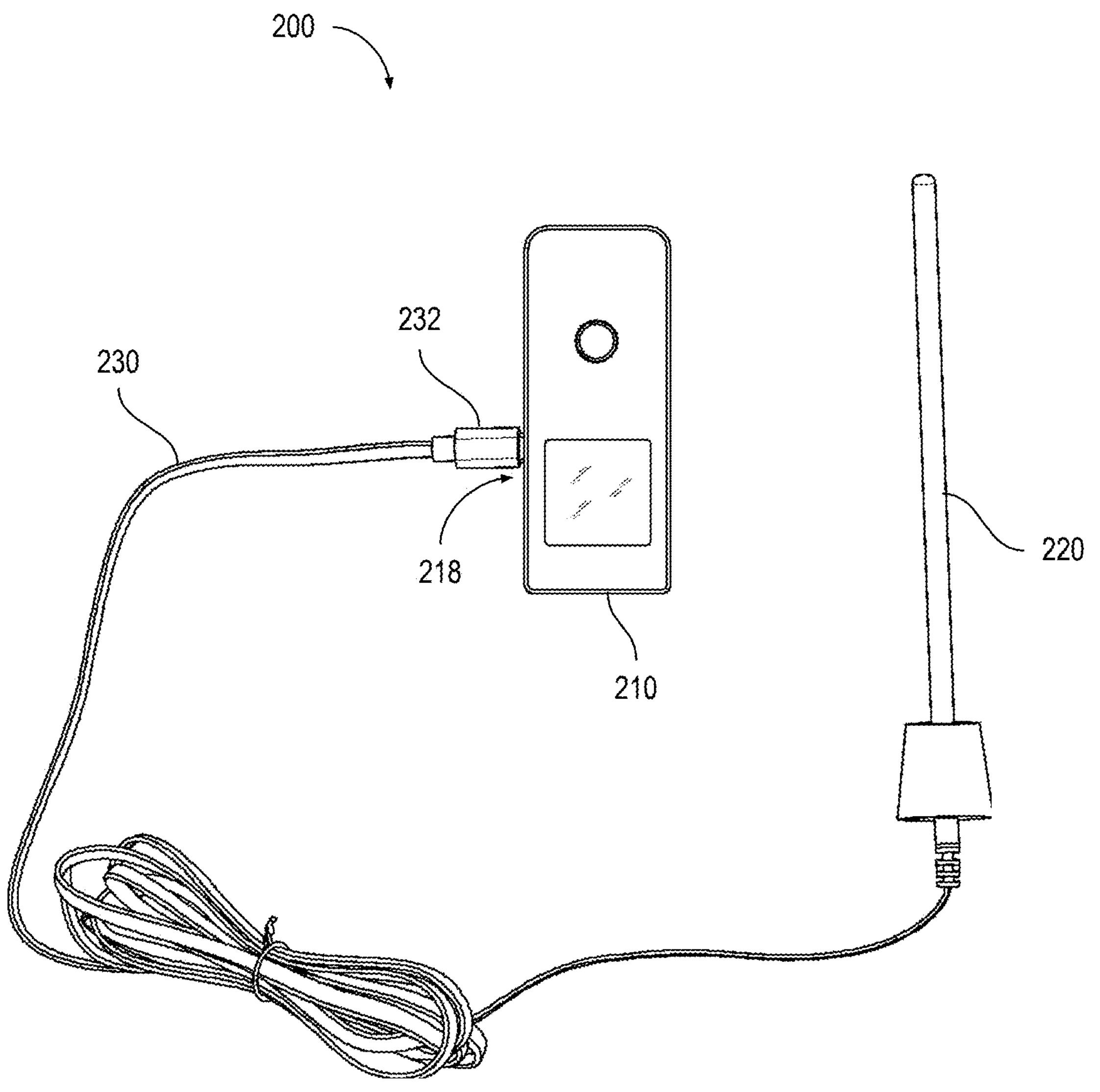
FIG. 2A illustrates a system for simultaneous monitoring of internal and ambient characteristics, according to one or more implementations herein.

FIG. 2A illustrates a system 200 for simultaneous monitoring of internal and ambient characteristics, according to one or more implementations herein. The system 200 may include temperature and humidity monitoring systems for monitoring both characteristics of internal content of a container (e.g., a wine bottle) as well as ambient environmental characteristics. The system 200 may monitor the internal and ambient characteristics for storage on a local device, as well as transmission over a network to a remote device. The system 200 may include an ambient sensing device 210 and a remote probe 220.

The ambient sensing device 210 may include an ambient temperature sensor, an ambient humidity sensor, a processor in electronic communication with the ambient temperature sensor and the ambient humidity sensor, and a networking device in electronic communication with the processor, the networking device configured to transmit data to a remote device via a network connection. The processor may be further configured to instruct the networking device to transmit an alert to the remote device. The alert may be sent following a triggering of an event determined by an event parameter.

The remote probe 220 may include a fluid temperature sensor and a fitting configured to secure the remote probe to a container such that the fluid temperature sensor is disposed within the container in thermal communication with a fluid disposed within the container. The remote probe 220 may be configured such that the fluid temperature sensor is in removable electronic communication with the processor, for example, via a cable 230 connecting via a plug 232 to a data port 218 of the ambient sensing device 210. The fitting may include a stopper, which may be configured for insertion into a neck of a bottle. The fitting may be further defined by a through hole, which may have a circumdiameter such that a probe extension comprising the fluid temperature sensor may be insertably disposed therethrough.

The data may include one or more of an ambient temperature measurement measured by the ambient temperature sensor, a fluid temperature measurement measured by the fluid temperature sensor, or an ambient humidity measurement measured by the ambient humidity sensor. In some implementations, the data includes an ambient temperature measurement measured by the ambient temperature sensor, a fluid temperature measurement measured by the fluid temperature sensor, and an ambient humidity measurement measured by the ambient humidity sensor. The data may include an alert.

The ambient sensing device 210 may include an electronic storage unit in electronic communication with the processor. The processor may be configured to store the data on the electronic storage unit.

The processor may be configured to retrieve the data stored on the electronic storage unit and instruct the networking device to transmit the data to the remote device. This may be done after the network connection is established.

The processor may be further configured to receive a transmission schedule from the remote device, store the transmission schedule on the electronic storage unit, and transmit the data via the networking device to the remote device according to the transmission schedule. The transmission schedule may be a function of an event parameter (e.g., an ambient temperature threshold, an ambient humidity threshold, or a fluid temperature threshold).

The ambient sensing device 210 may further include an accelerometer in electronic communication with the processor. In such implementations, the data may further include an accelerometer measurement (e.g., motion/vibration detection) measured by the accelerometer.

The ambient sensing device 210 may further include a light sensor in electronic communication with the processor. In such implementations, the data may further include a light measurement measured by the light sensor.

The ambient sensing device 210 may further include an internal electrical power source (e.g., a battery). Such an internal electrical power source may be configured to power the system 200.

The ambient sensing device 210 may further include an electrical port configured to receive an electrical plug configured for delivery of electrical power from an external electrical power source. This electrical port may be, for example, coincident to or separate from the data port 218.

The processor may be further configured to, in response to a detected loss of electrical power at the electrical port, switch a power supply to the system 200 from the external electrical power source to the internal electrical power source. The processor may be further configured to, upon switching the power supply to the system 200, instruct the networking device to transmit a power status alert to the remote device.

The network connection may be a wireless network connection (e.g., a cellular network connection or a local area network connection). The processor may be configured to select one of a cellular network connection or a local area network connection (e.g., via WIFI®) as the network connection based on one or more of a signal strength comparison or user input. The device may either be preprogrammed or configured by the user to prefer one mode of connection (e.g., cellular or local area network) over the other, thus defaulting to the preferred connection mode and reserving the other connection mode as a backup.

The ambient sensing device 210 may include a display in electronic communication with the processor. The display may be configured to display the data.

The ambient sensing device 210 may in some implementations be configured with multiple data ports 218, each for connection to a different remote probe 220. In such an implementation, the ambient sensing device 210 may operate as a hub for multiple remote probes 220.

Figure 2B:
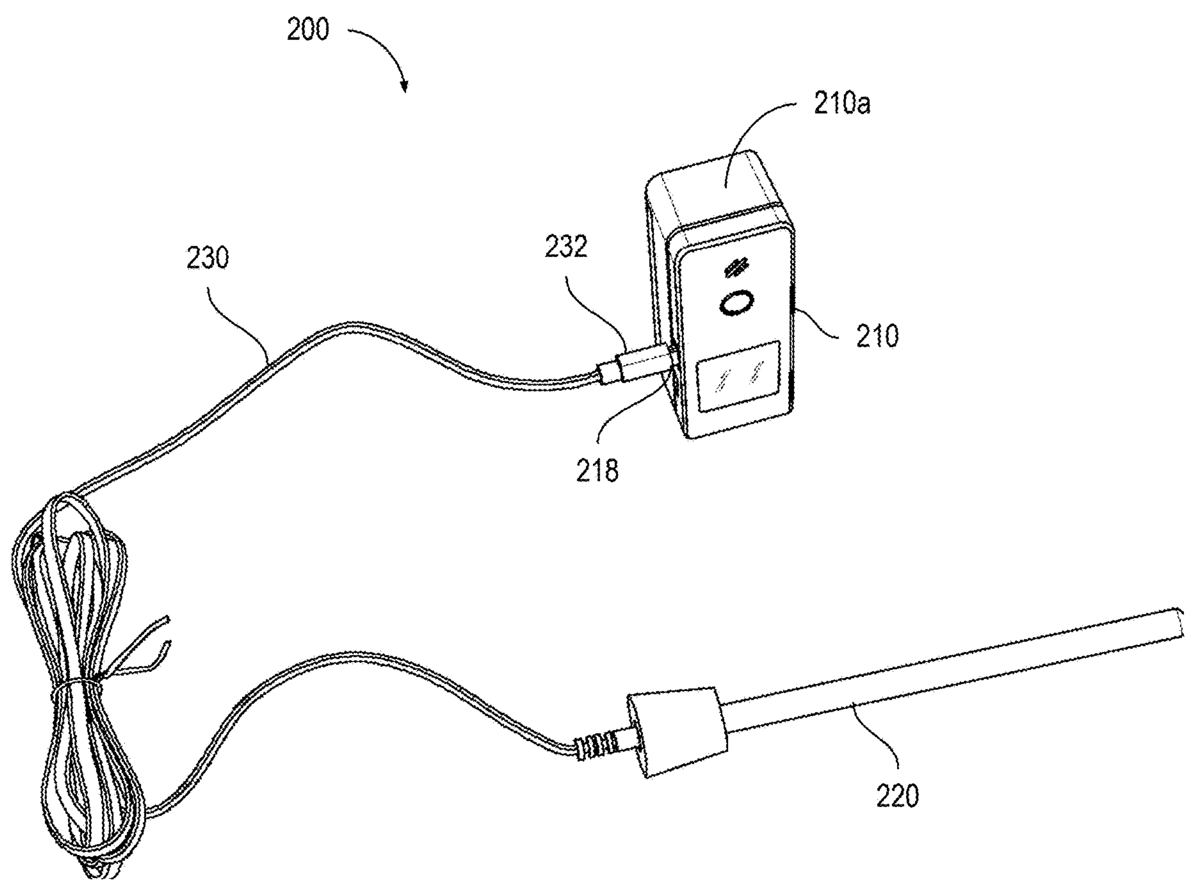
FIG. 2B illustrates a perspective view of the system for simultaneous monitoring of internal and ambient characteristics, according to one or more implementations herein.

FIG. 2B illustrates a perspective view of the system 200 for simultaneous monitoring of internal and ambient characteristics, according to one or more implementations herein. In addition to those aspects discussed in relation to FIG. 2A and incorporated here, FIG. 2B illustrates a housing 210*a* of the ambient sensing device 210. The housing 210*a* may be configured for removable disposing of the battery to power the system 200.

Figure 3A:
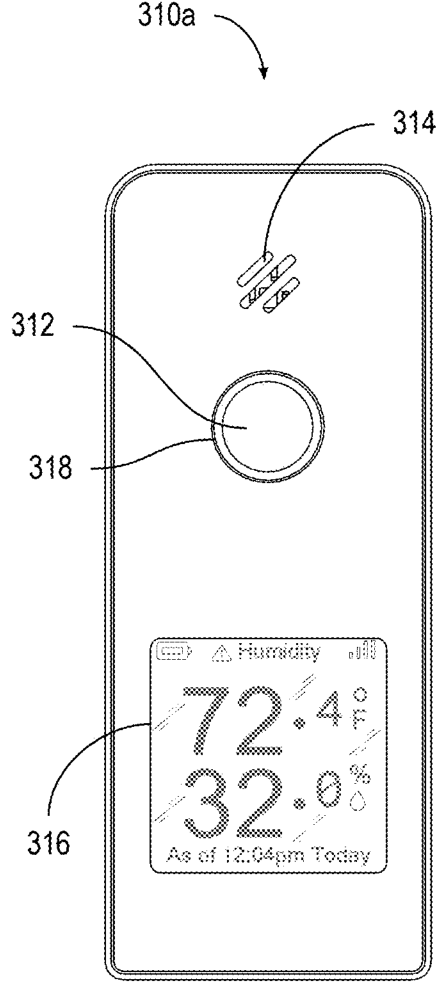
FIG. 3A illustrates an ambient sensing device with a display, according to one or more implementations herein.

FIG. 3A illustrates an ambient sensing device 310*a* with a display 316, according to one or more implementations herein. The ambient sensing device 310*a* may include an ambient sensor access cutout 314, which may permit exposure of sensors disposed within the ambient sensing device 310*a* to the environment in which the ambient sensing device 310*a* is located, namely, air within that environment. In this way, sensors within the ambient sensing device 310*a* may be exposed to ambient air and thereby measure characteristics of that ambient air. For example, a temperature sensor disposed with the ambient sensing device 310*a* may be configured to measure an ambient temperature, a humidity sensor disposed with the ambient sensing device 310*a* may be configured to measure an ambient humidity, and a light sensor disposed with the ambient sensing device 310*a* may be configured to measure ambient light (e.g., luminance). In some implementations, the ambient sensing device 310*a* may include an accelerometer disposed therein configured to measure accelerations of the ambient sensing device 310*a*.

The ambient sensing device 310*a* may include a button 312. The button 312 may be configured for a variety of functions related to controlling the ambient sensing device 310*a*, including, for example, power on, power off, sleep, wake, BLUETOOTH® pairing, connect, disconnect, display on, display off, transmit, receive, menu select, option configuration, among other functions. Different functions may be accessible based on length of pushes, quantities of pushes, and or sequences of pushes of the button 312. In some implementations, there may be multiple buttons 312. Such implementations may perform at least some of the previously mentioned functions and other functions.

The ambient sensing device 310*a* may include a light 318, which may operate as a user indicator of state or function of the ambient sensing device 310*a*. The light 318 may in some implementations be a light ring disposed about the button 312.

Figure 3B:
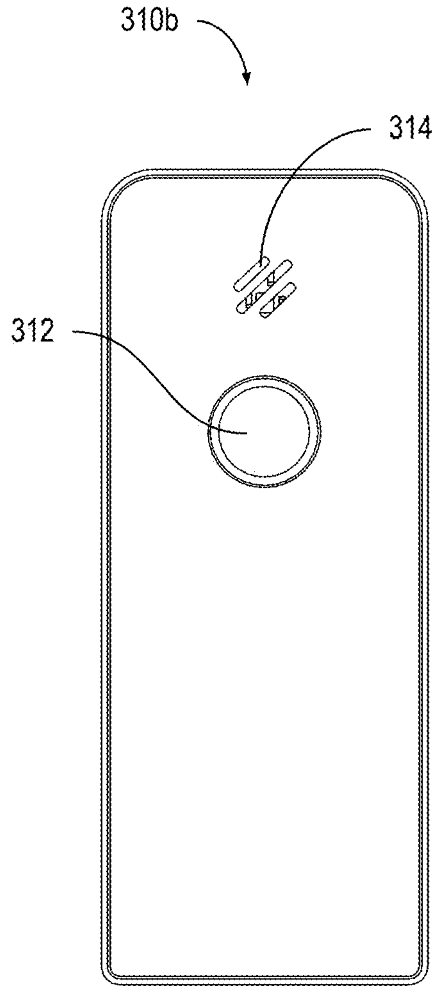
FIG. 3B illustrates an ambient sensing device without a display, according to one or more implementations herein.

FIG. 3B illustrates an ambient sensing device 310*b* without a display, according to one or more implementations herein. Some implementations of the ambient sensing device 310*b* may be configured without a display. In such implementations without a display, data may be accessed and viewed by a user on a remote device after the data is transferred from the ambient sensing device 310*b* to the remote device. Such implementations may include the ambient sensor access cutout 314 and the button 312.

Figure 3C:
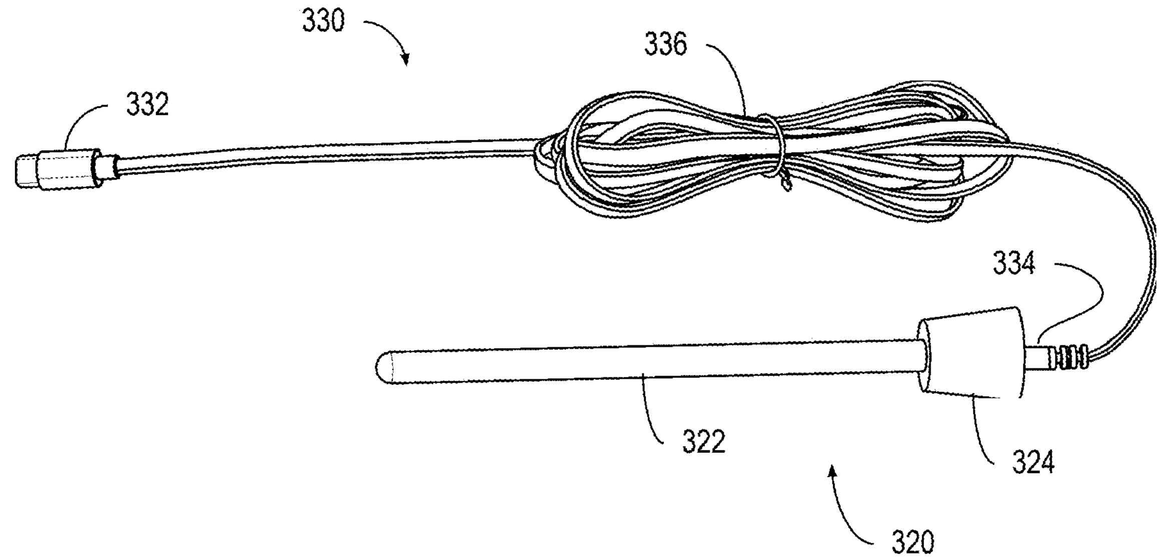
FIG. 3C illustrates a remote probe and wire connection, according to one or more implementations herein.

FIG. 3C illustrates a remote probe 320 and a cable 330, according to one or more implementations herein. The remote probe 320 and the cable 330 may enable measurement and monitoring of characteristics inside of a container, for recordable and processing by a device external to the container such as an ambient sensing device (e.g., the ambient sensing device 310*a* or the ambient sensing device 310*b*).

The remote probe 320 may include a fitting 324 and a probe extension 322. The fitting 324 may be configured to form an enclosure in an opening of a container by various means, including, for example, as a press-fit stopper, a screw-on cap, or a clamped fitting. In some implementations, the fitting 324 may be sized similarly to a wine bottle cork to provide for fitment of the remote probe 320 into the opening of a wine bottle.

The probe extension 322 may include a sensing apparatus for measuring a characteristic internal to a container. For example, the probe extension 322 may include a temperature sensor (e.g., a thermocouple or a thermistor) configured for measurement of a temperature within the container, or within media (e.g., a fluid) therein. In some implementations, the probe extension 322 may include a hardware module configured to digitize output from the sensing apparatus for transmission to the ambient sensing device. In some implementations, multiple sensing apparatuses measuring the same or different properties internal to the container may be disposed within the probe extension 322.

The cable 330 may be configured for transmission of signals between the remote probe 320 and an ambient sensing device. The cable 330 may connect to the remote probe 320 at a connection point 334 and may be configured for connection to an ambient sensing device via a plug 332. Between the plug 332 and the connection point 334 may be a wire 336 (e.g., shielded wire).

Figure 4:
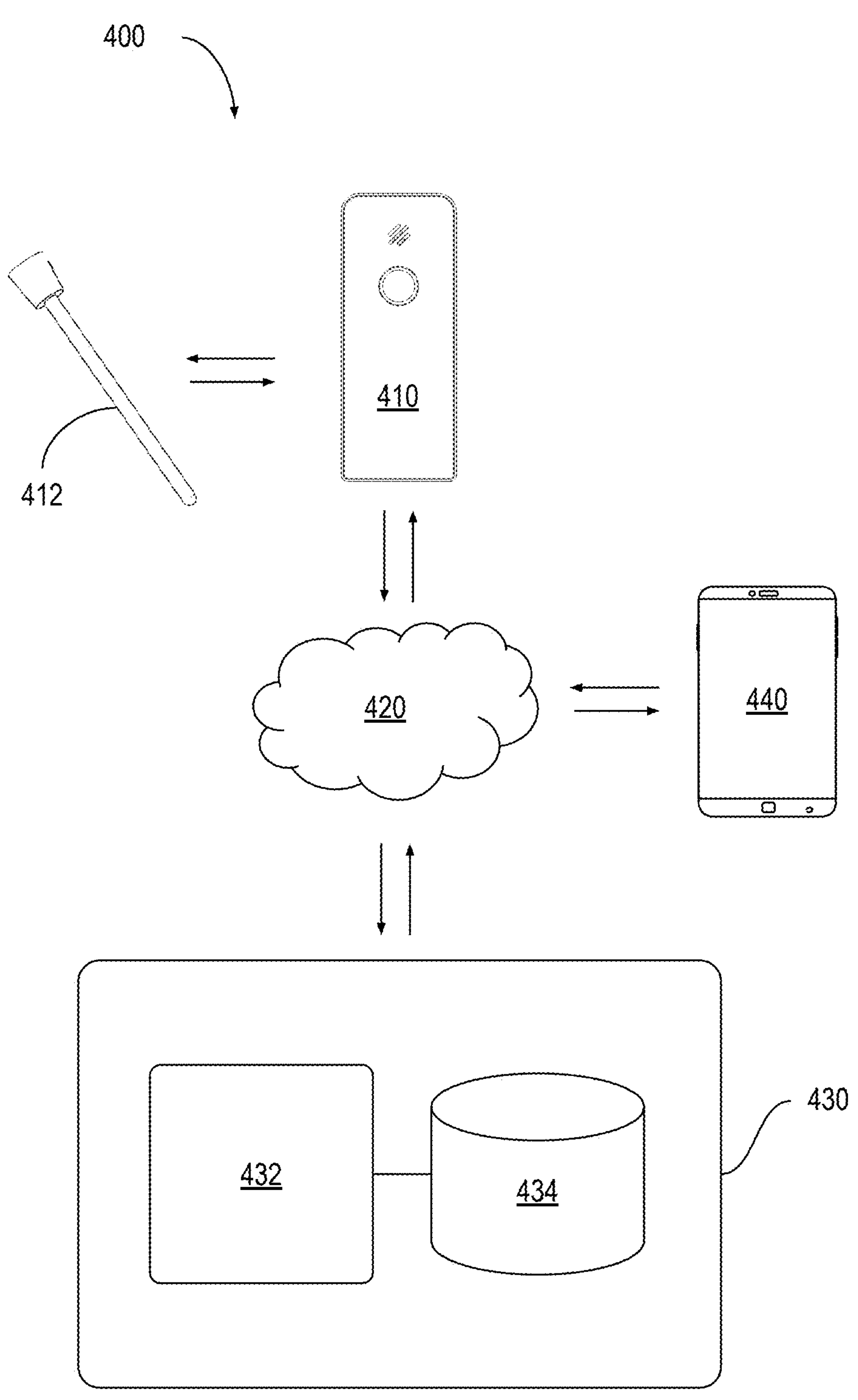
FIG. 4 Illustrates an operational environment, according to one or more of the implementations herein.

FIG. 4 Illustrates an operational environment 400, according to one or more of the implementations herein. As illustrated in FIG. 4, the operational environment 400 may include actors, including an ambient sensing device 410, a probe 412, a network 420, an application server 430 having at least a computing resource 432 and a storage 434, and a remote device 440.

The ambient sensing device 410 may include any variety of devices a user may use to interface with the application server 430 via the network 420, including, for example, a server, a desktop computer, a laptop computer, a handheld computer, a tablet computing platform, a Netbook, a Smartphone, a gaming console, and/or other computing platforms.

The probe 412 may include, for example, a temperature probe. The probe 412 may be configured to be disposed within a container (e.g., a wine bottle, buffer bottle, canister, etc.) while maintaining a seal thereto.

The network 420 may include any variety of devices configured to enable a device to communicate with other devices, such as via a wired connection and/or a wireless connection, for example, via the internet and/or other networks using, for example, TCP/IP or cellular hardware enabling wired or wireless (e.g., cellular, 2G, 3G, 4G, 4G LTE, 5G, 6G, BLUETOOTH®, Long Range (LORA®) or WIFI®) communication. For example, the network 420 may include, for example, a receiver, a transmitter, a transceiver, a modem, a network interface card, and/or an antenna.

It will be understood that one or more ambient sensing devices 410 may be grouped together and connected to a hub device. The hub device may either be an ambient sensing device 410 or a discrete hub device configured to perform at least some of the communication functions over the network 420. In this way, multiple ambient sensing devices 410 may be connected to the hub device with local connectivity protocol (e.g., BLUETOOTH®, Long Range (LORA®) or WIFI®), and data from one or all of the ambient sensing devices 410 may be exchanged over the network 420 by the hub device. In this way, a single wireless internet network connection may be used to receive data from or control multiple ambient sensing devices 410.

The application server 430 may include any variety of devices configurable to perform the implementations and methods disclosed herein and interface with the ambient sensing device 410 via the network 420, including, for example, a server, a desktop computer, a laptop computer, a handheld computer, a tablet computing platform, a Netbook, a Smartphone, a gaming console, and/or other computing platforms.

The application server 430 may include the computing resource 432. The computing resource 432 may include, for example, one or more processor(s) configured to execute machine-readable instructions for implementing all or some of the implementations herein. The computing resource 432 may be configured to access the storage 434 to retrieve and/or write electronic data from and to the storage 434.

The application server 430 may include the storage 434. The storage 434 may be configured to electronically store data (e.g., host) corresponding to one or more databases or other forms of data storage for use in implementations herein. The storage 434 may be accessible by the computing resource 432.

The remote device 440 may include any variety of devices a user may use to interface with the application server 430 via the network 420, including, for example, a server, a desktop computer, a laptop computer, a handheld computer, a tablet computing platform, a Netbook, a Smartphone, a gaming console, and/or other computing platforms.

Figure 5:
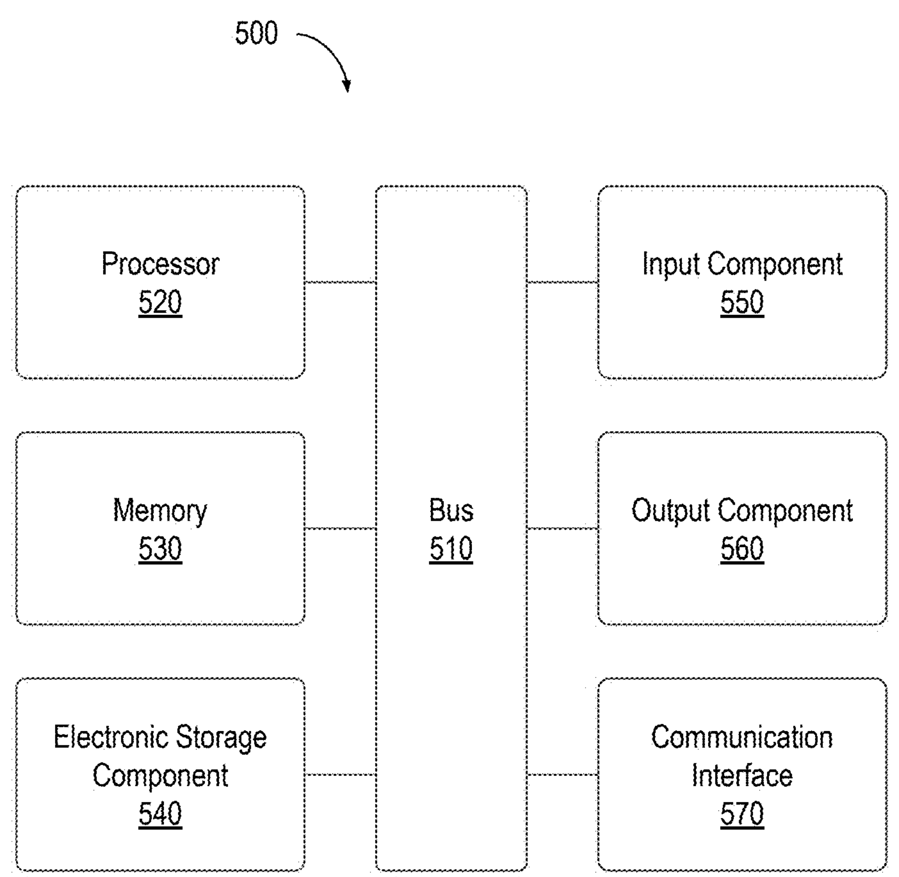
FIG. 5 is a diagram of example components of a device, according to one or more implementations herein.

FIG. 5 is a diagram of example components of a device 500, according to one or more implementations herein. The device 500 may correspond to one or more devices, network, resource, or service of FIG. 1-4 or 6-10. In some implementations, one or more device, network, resource, or service of FIG. 1-4 or 6-10 may include one or more of the devices 500 and/or one or more components of the device 500, for example, according to a client/server architecture, a peer-to-peer architecture, and/or other architectures, which may include a plurality of hardware, software, and/or firmware components operating together to provide the functionality attributed herein to the device 500. In some implementations, the device 500 may include a distributed computing architecture (e.g., one or more individual computing platforms operating in concert to accomplish a computing task). For example, the device 500 may be implemented by a cloud of computing platforms operating together as the device 500. By way of non-limiting example, a given device 500 may include one or more of a server, a desktop computer, a laptop computer, a handheld computer, a tablet computing platform, a Netbook, a Smartphone, a gaming console, and/or other computing platforms.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

The device 500 may include a bus 510, a processor 520, a memory 530, a storage component 540, an input component 550, an output component 560, and a communication component 570.

The bus 510 includes a component that enables wired and/or wireless communication among the components of device 500. The bus 510 may enable various components of a computer system to communicate with each other, allowing for the transfer of data from one part to another.

The processor 520 may include a central processing unit, a graphics processing unit, a microprocessor, a controller, a microcontroller, a digital signal processor, a field-programmable gate array (FPGA), an application-specific integrated circuit, and/or another type of processing component. The processor 520 may be implemented in hardware, firmware, or a combination of hardware and software. In some implementations, the processor 520 may include one or more processors capable of being programmed to perform a function. Such processors may or may not be all integral to the same physical device and may in some embodiments be distributed among several devices.

The processor 520 may be configured to execute one or more of the modules disclosed herein, and/or other modules by software; hardware; firmware; some combination of software, hardware, and/or firmware; and/or other mechanisms for configuring processing capabilities on the processor 520. As used herein, the term "module" may refer to any component or set of components that perform the functionality attributed to the module. This may include one or more physical processors during execution of processor readable instructions, the processor readable instructions, circuitry, hardware, storage media, or any other components. Various modules or portions thereof may be implemented in any of various ways, including procedure-based techniques, component-based techniques, and/or object-oriented techniques, among others. For example, the program instructions may be implemented using system libraries, language libraries, model-view-controller (MVC) principles, application programming interfaces (APIs), system-specific programming languages and principles, cross-platform programming languages and principles, pre-compiled programming languages, markup programming languages, stylesheet languages, "bytecode" programming languages, object-oriented programming principles or languages, other programming principles or languages, C, C++, C#, Java, JavaScript, Python, PHP, HTML, CSS, TypeScript, R, Elm, Unity, VB.Net, Visual Basic, Swift, Objective-C, Perl, Ruby, Go, SQL, Haskell, Scala, Arduino, assembly language, Microsoft Foundation Classes (MFC), Streaming SIMD Extension (SSE), or other technologies or methodologies, as desired.

It should be appreciated that although some modules disclosed herein may be illustrated for example as being implemented within a single processing unit, in embodiments in which the processor 520 includes multiple processing units, one or more of modules disclosed herein may be implemented remotely from the other modules. The description of the functionality provided by the different modules disclosed herein is for illustrative purposes, and is not intended to be limiting, as any of modules described herein may provide more or less functionality than is described. For example, one or more of modules disclosed herein may be eliminated, and some or all of its functionality may be provided by other ones of modules disclosed herein. As another example, the processor 520 may be configured to execute one or more additional modules that may perform some or all of the functionality attributed herein to one of modules disclosed herein.

The memory 530 may include a random-access memory, a read only memory, and/or another type of memory (e.g., a flash memory, a magnetic memory, and/or an optical memory).

The electronic storage component 540 may store information and/or software related to the operation of the device 500. For example, the electronic storage component 540 may include a solid-state disk drive, a hard disk drive, a magnetic disk drive, an optical disk drive, a compact disc, a digital versatile disc, and/or another type of non-transitory computer-readable medium. Implementations of the electronic storage component 540 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Implementations of the electronic storage component 540 may include one or both of system storage provided integrally (i.e., substantially non-removable) to the device 500 and/or removable storage that is removably connectable to the device 500 via, for example, a data port (e.g., a serial port, a USB port, an IEEE 1394 port, a THUNDERBOLT™ port, etc.) or a drive (e.g., disk drive, flash drive, or solid-state drive etc.). The electronic storage component 540 may also or alternatively include one or more virtual storage resources (e.g., cloud storage, a virtual private network, and/or other virtual storage resources). An electronic storage may store software algorithms, information determined by one or more processors, information received from one or more computing platforms, information received from one or more remote platforms, databases (e.g., structured query language (SQL) databases (e.g., MYSQL®, MARIADB®, MONGODB®), NO-SQL databases, among others), data files, compiled data, analyzed data, charts, tables, videos, images, presentations, and 3D content in the respective format and/or other information enabling a computing platform to function as described herein.

The input component 550 may enable the device 500 to receive input, such as user input and/or sensed inputs. For example, the input component 550 may include a touch screen, a keyboard, a keypad, a mouse, a button, a microphone, a switch, a sensor (internal and/or external), a global positioning system component, an accelerometer, a gyroscope, and/or an actuator.

The output component 560 may enable the device 500 to provide output, such as via a display, a speaker, and/or one or more light-emitting diodes.

The communication component 570 may enable the device 500 to communicate with other devices, such as via a wired connection and/or a wireless connection, for example, via the internet and/or other networks using, for example, TCP/IP or cellular hardware enabling wired or wireless (e.g., cellular, 2G, 3G, 4G, 4G LTE, 5G, WIFI®, near field communication (NFC), BLUETOOTH®) communication. For example, the communication component 570 may include a receiver, a transmitter, a transceiver, a modem, a network interface card, and/or an antenna.

As used herein, "internet" may include an interconnected network of systems and a suite of protocols for the end-to-end transfer of data therebetween. A model describing may be the Transport Control Protocol and Internet Protocol (TCP/IP), which may also be referred to as the internet protocol suite. TCP/IP provides a model of four layers of abstraction: an application layer, a transport layer, an internet layer, and a link layer. The link layer may include hosts accessible without traversing a router, and thus may be determined by the configuration of the network (e.g., a hardware network implementation, a local area network, a virtual private network, or a networking tunnel). The link layer may be used to move packets of data between the internet layer interfaces of different hosts on the same link. The link layer may interface with hardware for end-to-end transmission of data. The internet layer may include the exchange of datagrams across network boundaries (e.g., from a source network to a destination network), which may be referred to as routing, and is performed using host addressing and identification over an internet protocol (IP) addressing system (e.g., IPv4, IPV6). A datagram may include a self-contained, independent, basic unit of data, including a header (e.g., including a source address, a destination address, and a type) and a payload (e.g., the data to be transported), to be transferred across a packet-switched network. The transport layer may utilize the user datagram protocol (UDP) to provide for basic data channels (e.g., via network ports) usable by applications for data exchange by establishing end-to-end, host-to-host connectivity independent of any underlying network or structure of user data. The application layer may include various user and support protocols used by applications users may use to create and exchange data, utilize services, or provide services over network connections established by the lower layers, including, for example, routing protocols, the hypertext transfer protocol (HTTP), the file transfer protocol (FTP), the simple mail transfer protocol (SMTP), and the dynamic host configuration protocol (DHCP). Such data creation and exchange in the application layer may utilize, for example, a client-server model or a peer-to-peer networking model. Data from the application layer may be encapsulated into UDP datagrams or TCP streams for interfacing with the transport layer, which may then effectuate data transfer via the lower layers.

The communication component 570 may further implement an internet-of-things ("IoT") configuration, which may include a network of physical objects-devices, vehicles, buildings, and other items-embedded with electronics, software, sensors, and network connectivity that enables these objects to collect and exchange data via the Internet. Each IoT product/device may be an endpoint device having its own Internet address (e.g., IPV4, IPV6 address). The IoT allows objects to be sensed and controlled remotely across an existing network infrastructure (e.g., the Internet), creating opportunities for more direct integration of the physical world into computer-based systems.

The device 500 may perform one or more processes described herein. For example, a non-transitory computer-readable medium (e.g., the memory 530 and/or the storage component 540) may store a set of instructions (e.g., one or more instructions, code, software code, and/or program code) for execution by the processor 520. The processor 520 may execute the set of instructions to perform one or more processes described herein. In some implementations, execution of the set of instructions, by one or more processors 520, causes the one or more processors 520 and/or the device 500 to perform one or more processes described herein. In some implementations, hardwired circuitry may be used instead of or in combination with the instructions to perform one or more processes described herein. Thus, implementations described herein are not limited to any specific combination of hardware circuitry and software.

The number and arrangement of components shown in FIG. 5 are provided as an example. The device 500 may include additional components, fewer components, different components, or differently arranged components than those shown in FIG. 5. Additionally, or alternatively, a set of components (e.g., one or more components) of the device 500 may perform one or more functions described as being performed by another set of components of the device 500.

In addition to the example configuration described herein in FIG. 5, various steps, functions, and/or operations of the device 500 and the methods disclosed herein may be carried out by one or more of, for example, electronic circuits, logic gates, multiplexers, programmable logic devices, ASICs, analog or digital controls/switches, microcontrollers, or computing systems. Program instructions implementing methods such as those described herein may be transmitted over or stored on carrier medium. The carrier medium may include a storage medium such as a read-only memory, a random-access memory, a magnetic or optical disk, a non-volatile memory, a solid-state memory, a magnetic tape, and the like. A carrier medium may include a transmission medium such as a wire, cable, or wireless transmission link.

Figure 6:
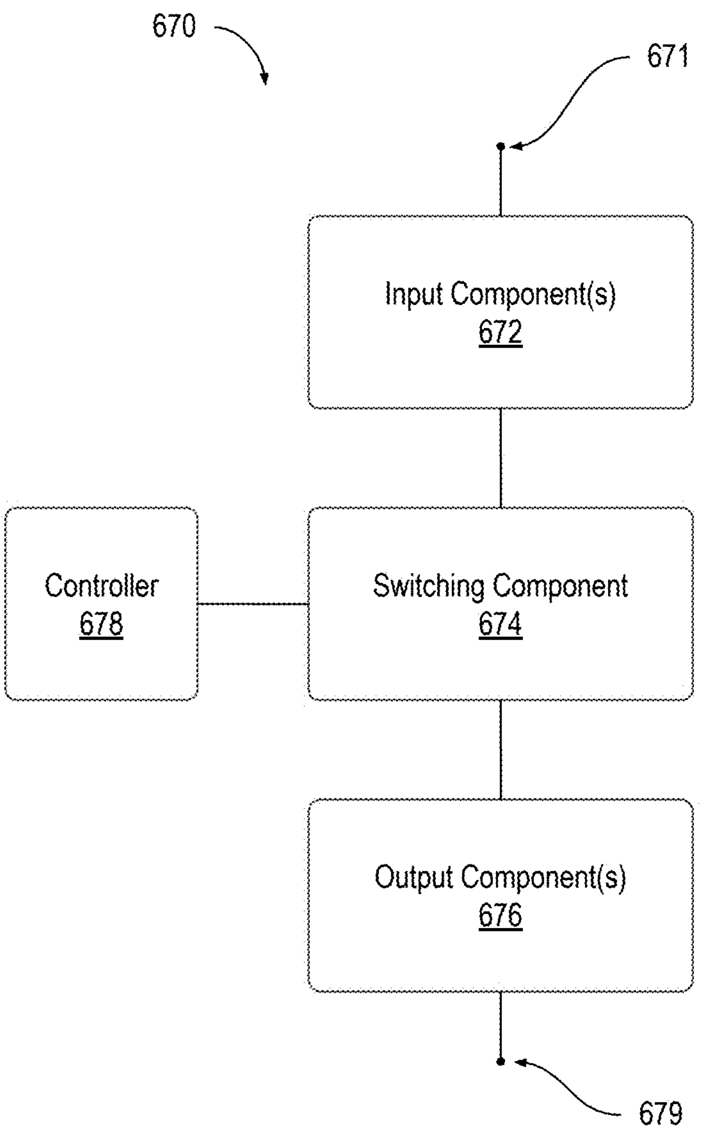
FIG. 6 is a diagram of example components of a device.

FIG. 6 is a diagram of example components of a device 670, according to one or more implementations herein. The device 670 may correspond to the communication component 570, the network interface 770, or the network interface 970. In some implementations, the communication component 570, the network interface 770, or the network interface 970 may include one or more of the devices 670 and/or one or more components of the device 670. As shown in FIG. 6, the device 670 may include one or more input components 672 (herein referred to collectively as the input components 672 or individually as the input component 672), a switching component 674, one or more output components 676 (herein referred to collectively as the output components 676 or individually as the output component 676), and a controller 678.

The input component 672 may be one or more points of attachment for one or more input physical links 671 (herein referred to collectively as the input physical links 671 or individually as the input physical link 671) and include one or more points of entry for incoming traffic, such as packets. The input component 672 may process incoming traffic, such as by performing data link layer encapsulation or decapsulation. In some implementations, the input component 672 may transmit and/or receive packets. In some implementations, the input component 672 may include an input line card that includes one or more packet processing components (e.g., in the form of integrated circuits), such as one or more interface cards (IFCs), packet forwarding components, line card controller components, input ports, processors, memories, and/or input queues. In some implementations, the device 670 may include one or more of the input components 672.

The switching component 674 may interconnect the input components 672 with the output components 676. In some implementations, the switching component 674 may be implemented via one or more crossbars, via buses, and/or with shared memories. The shared memories may act as temporary buffers to store packets from the input components 672 before the packets are eventually scheduled for delivery to the output components 676. In some implementations, the switching component 674 may enable the input components 672, the output components 676, and/or the controller 678 to communicate with one another.

The output component 676 may store packets and may schedule packets for transmission on the output physical link(s) 679 (herein referred to collectively as the output physical links 679 or individually as the output physical link 679). The output component 676 may support data link layer encapsulation or decapsulation, and/or a variety of higher-level protocols. In some implementations, the output component 676 may transmit packets and/or receive packets. In some implementations, the output component 676 may include an output line card that includes one or more packet processing components (e.g., in the form of integrated circuits), such as one or more IFCs, packet forwarding components, line card controller components, output ports, processors, memories, and/or output queues. In some implementations, the device 670 may include one or more output components 676. In some implementations, the input component 672 and the output component 676 may be implemented by the same set of components (e.g., an input/output component may be a combination of the input component 672 and the output component 676).

The controller 678 includes a processor in the form of, for example, a CPU, a GPU, an APU, a microprocessor, a microcontroller, a DSP, an FPGA, an ASIC, and/or another type of processor. The processor is implemented in hardware, firmware, or a combination of hardware and software. In some implementations, the controller 678 may include one or more processors that can be programmed to perform a function.

In some implementations, the controller 678 may include a RAM, a ROM, and/or another type of dynamic or static storage device (e.g., a flash memory, a magnetic memory, an optical memory, etc.) that stores information and/or instructions for use by the controller 678.

In some implementations, the controller 678 may communicate with other devices, networks, and/or systems connected to the device 670 to exchange information regarding network topology. The controller 678 may create routing tables based on the network topology information, may create forwarding tables based on the routing tables, and may forward the forwarding tables to the input components 672 and/or the output components 676. The input components 672 and/or the output components 676 may use the forwarding tables to perform route lookups for incoming and/or outgoing packets.

The controller 678 may perform one or more processes described herein. The controller 678 may perform these processes in response to executing software instructions stored by a non-transitory computer-readable medium. A computer-readable medium is defined herein as a non-transitory (e.g., the medium itself (i.e., tangible, not a signal) as opposed to a limitation on data storage persistency (e.g., RAM vs. ROM) memory device. A memory device includes memory space within a single physical storage device or memory space spread across multiple physical storage devices.

Software instructions may be read into a memory and/or storage component associated with the controller 678 from another computer-readable medium or from another device via a communication interface. When executed, software instructions stored in a memory and/or storage component associated with the controller 678 may cause the controller 678 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 6 are provided as an example. In practice, the device 670 may include additional components, fewer components, different components, or differently arranged components than those shown in FIG. 6. Additionally, or alternatively, a set of components (e.g., one or more components) of the device 670 may perform one or more functions described as being performed by another set of components of the device 670.

Figure 7:
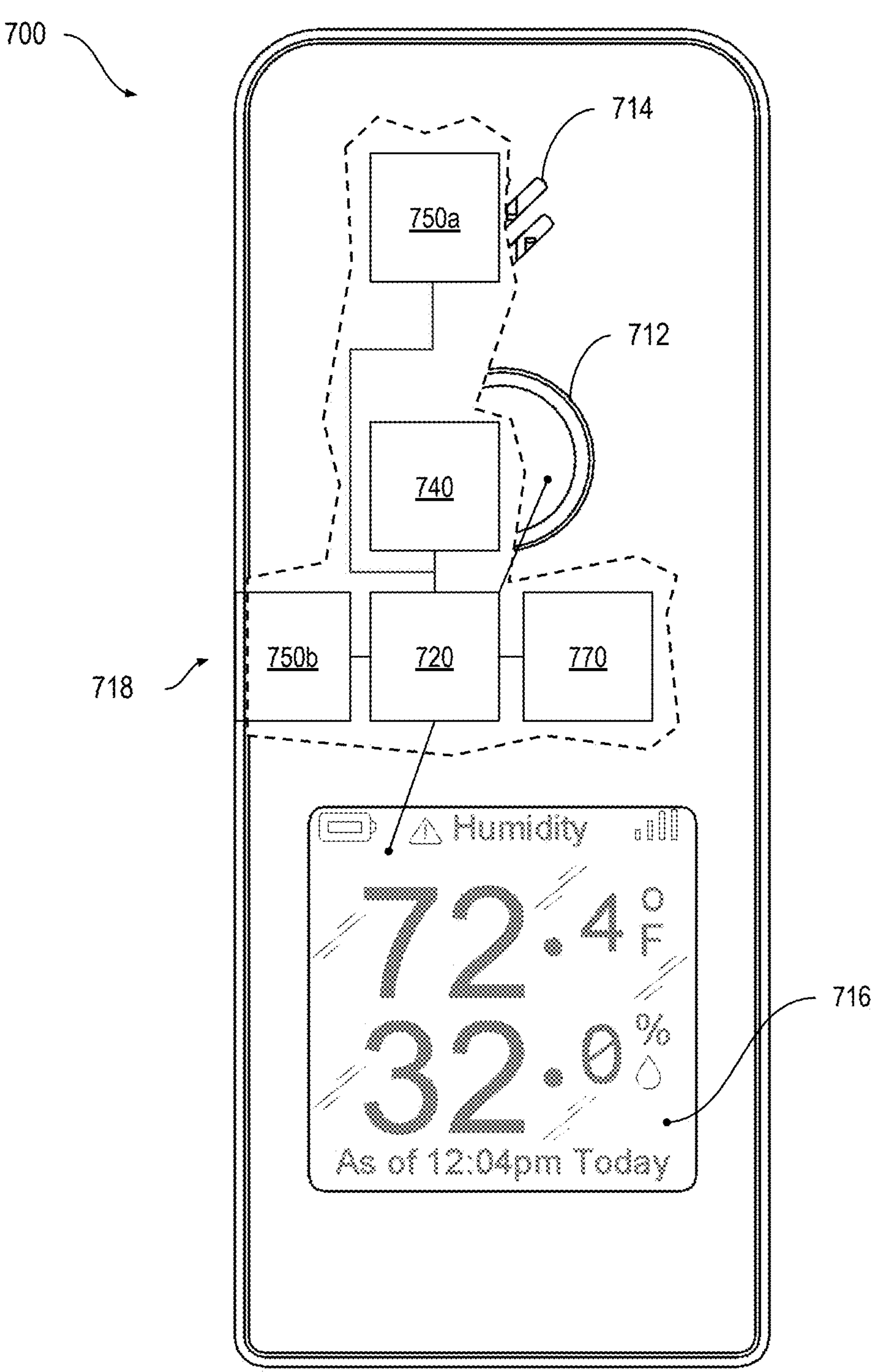
FIG. 7 illustrates example components of a device, according to one or more implementations herein.

FIG. 7 illustrates example components of an ambient sensing device 700, according to one or more implementations herein. The ambient sensing device 700 or components thereof may correspond to a temperature and humidity monitoring system (e.g., such as, for example, the ambient sensing device 110, the ambient sensing device 210, the ambient sensing device 310*a*, the ambient sensing device 310*b*, the ambient sensing device 410, or the device 500), or other devices for implementing the methods and systems herein or components thereof. While in FIG. 7, the ambient sensing device 700 is depicted as a wireless temperature and humidity sensing device, it will be understood that the ambient sensing device 700 may include various devices, such as, for example, one or more other computing platforms.

The ambient sensing device 700 may be configured to communicate with other devices or remote platforms via one or more devices such as the device 500 or the device 670, and/or according to a client/server architecture, a peer-to-peer architecture, and/or other architectures.

The ambient sensing device 700 may include various components, all, or some of which may be used in operation or use of the ambient sensing device 700. Such components may include, for example, one or more processors 720, one or more electronic storages 740, one or more network interfaces 770, or one or more peripheral or input/output components, including displays, buttons, cameras, speakers, or microphones. It will be understood that not all of these components are required for every embodiment of the ambient sensing device 700, and there may be more than one of any given components in various embodiments of the ambient sensing device 700.

The ambient sensing device 700 may include one or more processors configured to execute computer program modules. The computer program modules may be configured to enable a user associated with the ambient sensing device 700 to interface with a system, (e.g., similar to the device 500) and/or external resources, and/or provide other functionality attributed herein to the ambient sensing device 700.

The ambient sensing device 700 may include the electronic storage 740, one or more processors 720, and/or other components. The ambient sensing device 700 may include communication lines, or ports to enable the exchange of information with a network and/or other computing platforms (e.g., the network interface 770). Illustration of the ambient sensing device 700 in FIG. 7 is not intended to be limiting. The ambient sensing device 700 may include a plurality of hardware, software, and/or firmware components operating together to provide the functionality attributed herein to the ambient sensing device 700. For example, the ambient sensing device 700 may be implemented by a cloud of computing platforms operating together as the ambient sensing device 700.

The electronic storage 740 (herein referred to collectively as the electronic storages 740 or individually as the electronic storage 740) may be directly or indirectly in operative electronic communication with the processor 720 may comprise non-transitory storage media that electronically stores information. The electronic storage media of the electronic storage 740 may include one or both of system storage that is provided integrally (i.e., substantially non-removable) with the ambient sensing device 700 and/or removable storage that is removably connectable to the ambient sensing device 700 via, for example, a data port (e.g., a USB port, an IEEE 1394 port, a THUNDERBOLT™ port, etc.) or a drive (e.g., a disk drive, flash drive, or solid-state drive etc.). The electronic storage 740 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash memory, etc.), and/or other electronically readable storage media. The electronic storage 740 may include one or more virtual storage resources (e.g., cloud storage, a virtual private network, and/or other virtual storage resources). The electronic storage 740 may store software algorithms, information determined by the processor 720, information received from the ambient sensing device 700, information received from the system or another remote platform, and/or other information that enables the ambient sensing device 700 to function as described herein.

The processor 720 (herein referred to collectively as the processors 720 or individually as the processor 720) may be configured to provide information processing capabilities in the ambient sensing device 700. As such, the processor 720 may include one or more of a digital processor, an analog processor, a digital circuit designed to process information, an analog circuit designed to process information, a state machine, and/or other mechanisms for electronically processing information. Although the processor 720 is shown in FIG. 7 as a single entity, this is for illustrative purposes only. In some embodiments, the processor 720 may include a plurality of processing units. These processing units may be physically located within the same device, or the processor 720 may represent processing functionality of a plurality of devices operating in coordination. The processor 720 may be configured to execute one or more of the modules disclosed herein, and/or other modules. The processor 720 may be configured to execute one or more of the modules disclosed herein, and/or other modules by software; hardware; firmware; some combination of software, hardware, and/or firmware; and/or other mechanisms for configuring processing capabilities on the processor 720. As used herein, the term "module" may refer to any component or set of components that perform the functionality attributed to the module. This may include one or more physical processors during execution of processor readable instructions, the processor readable instructions, circuitry, hardware, storage media, or any other components. Various modules or portions thereof may be implemented in any of various ways, including procedure-based techniques, component-based techniques, and/or object-oriented techniques, among others. For example, the program instructions may be implemented using ActiveX controls, model-view-controller (MVC) principles, application programming interfaces (APIs), system-specific programming languages and principles, cross-platform programming languages and principles, pre-compiled programming languages, "bytecode" programming languages, object-oriented programming principles or languages, other programming principles or languages, JavaBeans, Microsoft Foundation Classes (MFC), Streaming SIMD Extension (SSE), or other technologies or methodologies, as desired.

It should be appreciated that although the modules disclosed herein are illustrated in FIG. 7 as being implemented within a single processing unit, in embodiments in which the processor 720 includes multiple processing units, one or more of modules disclosed herein may be implemented remotely from the other modules. The description of the functionality provided by the different modules disclosed herein is for illustrative purposes, and is not intended to be limiting, as any of modules described herein may provide more or less functionality than is described. For example, one or more of modules disclosed herein may be eliminated, and some or all of its functionality may be provided by other ones of modules disclosed herein. As another example, the processor 720 may be configured to execute one or more additional modules that may perform some or all of the functionality attributed herein to one of modules disclosed herein.

The ambient sensing device 700 may be configured by machine-readable instructions. Such machine-readable instructions may include one or more instruction modules. The instruction modules may include computer program modules, which may be similar to, for example, at least a portion of the methods described herein. The instruction modules may include one or more of the modules and methods disclosed herein and/or other instruction modules and methods.

The network interface 770 (herein referred to collectively as the network interfaces 770 or individually as the network interface 770) may be directly or indirectly in operative electronic communication with, inter alia, the processor 720. The network interface 770 may operatively link the processor 720 and/or the ambient sensing device 700 with one or more other computing platforms, remote platforms, and/or external resources via one or more electronic communication links. For example, such electronic communication links may be established, at least in part, via a network such as the internet and/or other networks using, for example, TCP/IP or cellular hardware enabling wired or wireless (e.g., cellular, 2G, 3G, 4G, 4G LTE, 5G, or WIFI®) communication. It will be appreciated that this is not intended to be limiting, and that the scope of this disclosure includes embodiments in which the ambient sensing device 700, one or more other computing platforms, remote platforms, and/or external resources may be operatively linked via some other communication media.

The processor 720 may be directly or indirectly in operative electronic communication with one or more displays 716 (herein referred to collectively as the electronic storages 740 or individually as the electronic storage 740). The display 716 may include a device (or "hardware component") that displays "display data" to form an image or images, such as, but not limited to, a picture, text, a desktop background, a gaming background, a video, an application window etc. One example of the display 716 may include an integrated display. The display 716 may employ any appropriate display technology, such as for example, LCD flat panel, LED flat panel, flexible panels, etc., and may include other display hardware that may, as needed for a particular electronic device, be operatively coupled to other devices and components. Therefore, the display 716 may include display hardware such as, but not limited to, a frame buffer, hardware display drivers, etc. that store and refresh display data to be displayed by the display 716. Also, the display 716 may include integrated hardware for implementation of touchscreen functionality such that the display is operative to receive user input by touch or via a stylus.

The term "image" as used herein may refer generally to what is "displayed" on a display (e.g., the display 716 or the display 916) and which may be stored in memory as "display data." That is, an image may be displayed on a display by sending the appropriate display data to the display. Examples of images may include, but are not limited to, a background or "wallpaper," a photograph, an illustration, a chart, a graph, a table, a video, an application window, an icon, a widget, etc. In other words, the term "image" may refer to a background, or may refer individually, or collectively, to elements or objects in the foreground hovering over a background image such as wallpaper. The term "display data" may be used interchangeably herein with the term "image data" and refers to the information (data, or digital information) that the display interprets and/or decodes to show (i.e., to display) the user an image, as well as any associated elements or objects in the foreground of the background or wallpaper, etc.

The display 716 may present for visual inspection condition readings (e.g., temperature readings, humidity readings, battery level readings, connection strength readings, and alert readings), settings, and more.

The processor 720 may be directly or indirectly in operative electronic communication with one or more buttons 712 (herein referred to collectively as the face buttons 712 or individually as the face button 712). The button 712 may be configured to perform a variety of functions in relation to ambient sensing device 700.

The button 712 may be configured for a variety of functions related to controlling the ambient sensing device 700, including, for example, power on, power off, sleep, wake, BLUETOOTH® pairing, connect, disconnect, display on, display off, transmit, receive, menu select, option configuration, among other functions. Different functions may be accessible based on length of pushes, quantities of pushes, and or sequences of pushes of the button 712. In some implementations, there may be multiple buttons 712. Such implementations may perform at least some of the previously mentioned functions and other functions.

The processor 720 may be directly or indirectly in operative electronic communication with a sensor **750*a* (herein referred to collectively as the sensors 750*a* or individually as the sensor 750*a*), which may be in communication with an external environment via a sensor opening 714. The sensors 750*a* may include one or more of a temperature sensor (e.g., a thermocouple or thermistor), a humidity sensor (e.g., an electronic barometer), or a light sensor. It will be understood that the processor 720** may further be directly or indirectly in operative electronic communication with an accelerometer, however, the accelerometer need not be exposed to ambient air.

The processor 720 may be directly or indirectly in operative electronic communication with a data port interface **750*b* (herein referred to collectively as the port interfaces 750*b* or individually as the port interface 750*b*), which may be accessible by a port 718. The port interface may include one or more of a variety of port types (e.g., universal serial bus (USB), serial, etc.). The processor 720 or the port interface 750*b*** may be configured to determine whether a remote probe has been installed thereto and, if so, add data from the remote probe to the measured data.

Figure 8:
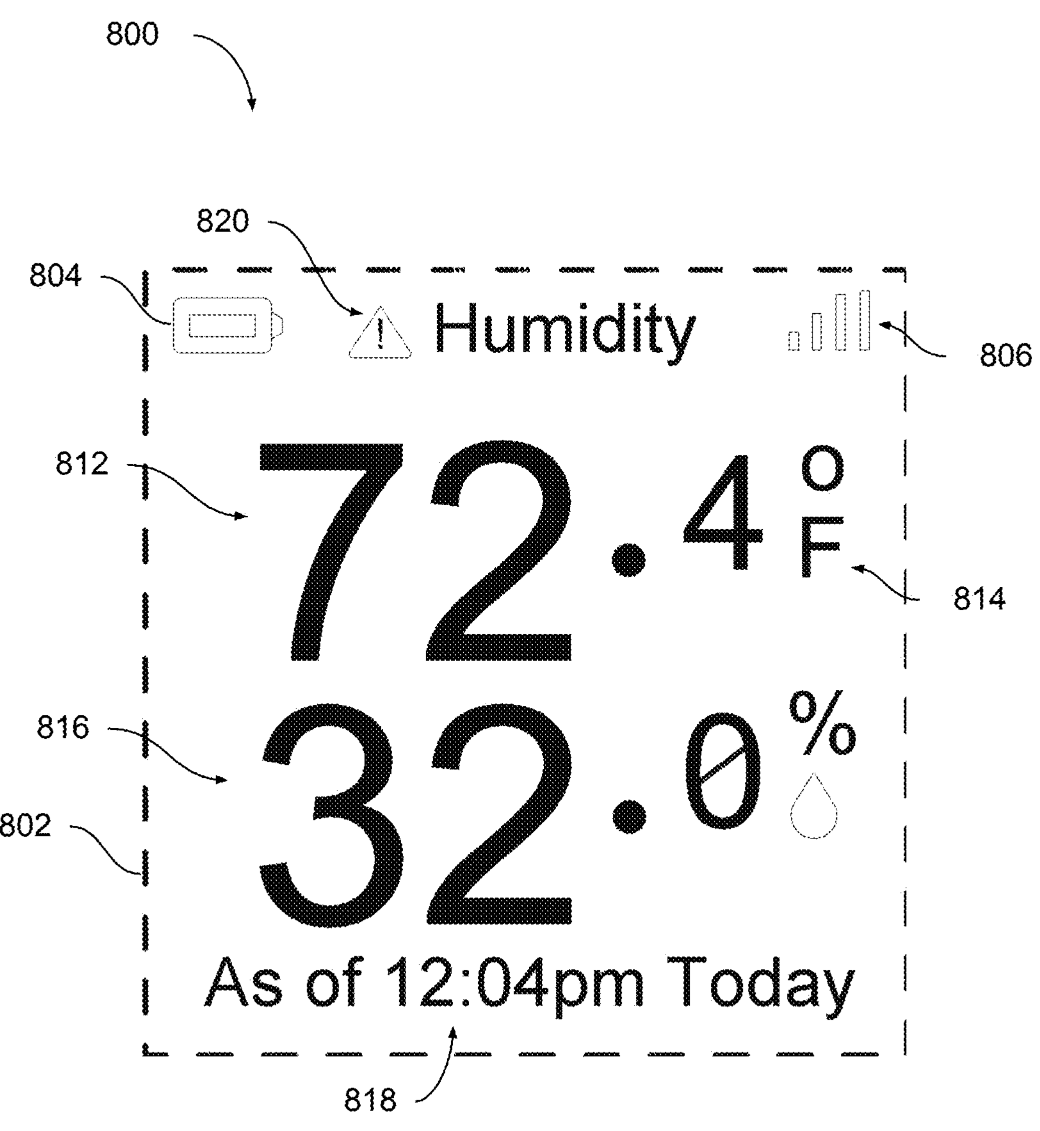
FIG. 8 illustrates a display presenting an example display interface, according to an embodiment.

FIG. 8 illustrates a display 800 presenting an example display interface 802, according to an embodiment. The display interface 802 may be displayed on a display similar to, for example the display 716 Accordingly, it will be understood that the particular presentation or arrangement shown in on the display interface 802 is not a limitation on the present disclosure. For example, various embodiments may be incorporated into different displays without departing from the present disclosure.

An interface module 804 may indicate a battery charge level of a battery configured to power the ambient sensing device and the remote probe. The interface module 804 may further indicate the state of the battery or power supply, for example, whether the battery is charging or at or below a threshold, or when the battery is not charging, or when the ambient sensing device is powered by an external power source and not a battery.

An interface module 806 may indicate a connection state, type, and/or strength. For example, the interface module 806 may display a signal strength for a WIFI® connection between the ambient sensing device and an external device (e.g., a remote device or a wireless networking router). The interface module 804 may further indicate if a connection interruption has occurred.

An interface module 812 may indicate a temperature, which may be, for example, a real-time temperature, an incremental temperature, or a threshold temperature. In some implementations, the interface module 812 may cycle through displaying various of these temperatures, and/or temperatures from other sensors. For example, the interface module 812 may alternate between displaying a real-time temperature reading from the ambient temperature sensor and a remote probe temperature sensor. An interface module 814 may indicate a unit of the temperature indicated by the interface module 812.

An interface module 816 may indicate a humidity, which may be, for example, a real-time humidity, an incremental humidity, or a threshold humidity. In some implementations, the interface module 816 may cycle through displaying various of these humidity readings, and/or humidity from other sensors. For example, the interface module 816 may alternate between displaying a real-time humidity reading from the ambient humidity sensor and a remote humidity sensor.

An interface module 818 may indicate a time corresponding to the indicated readings by the interface module 812 and/or the interface module 816.

An interface module 820 may indicate an alert, for example, whether a temperature, humidity, light, or acceleration has been measured above or below a given threshold.

Figure 9:
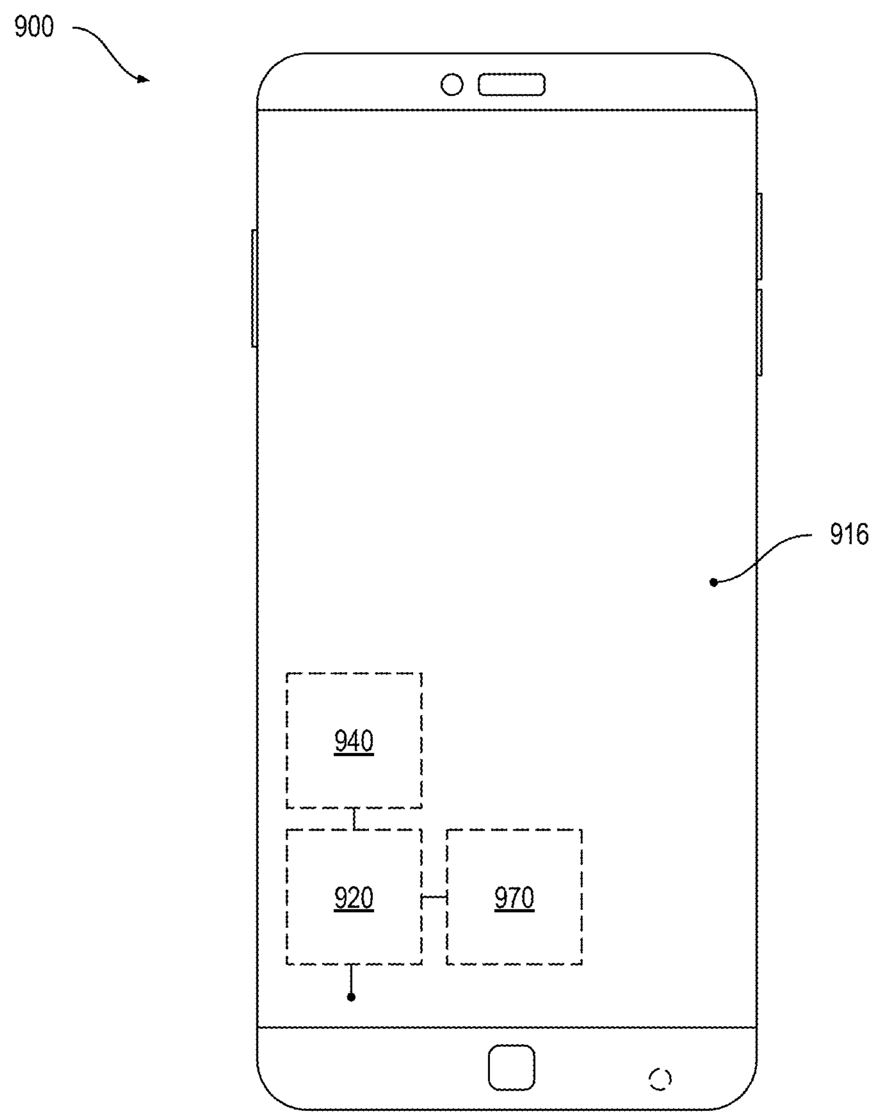
FIG. 9 illustrates example components of a device, according to one or more implementations herein.

FIG. 9 illustrates example components of a device 900, according to one or more implementations herein. The device 900 or components thereof may correspond to a remote device, or other devices for implementing the methods and systems herein or components thereof. While in FIG. 9, the device 900 is depicted as a smartphone, it will be understood that the device 900 may include various devices, such as, for example, one or more of a server, a desktop computer, a laptop computer, a handheld computer, a tablet computing platform, a Netbook, a Smartphone, a gaming console, and/or other computing platforms.

The device 900 may be configured to communicate with other devices or remote platforms via one or more devices such as the device 500 or the device 670, and/or according to a client/server architecture, a peer-to-peer architecture, and/or other architectures.

The device 900 may include various components, all, or some of which may be used in operation or use of the device 900. Such components may include, for example, one or more processors 920, one or more electronic storages 940, one or more network interfaces 970, or one or more peripheral or input/output components, including displays, buttons, cameras, speakers, or microphones. It will be understood that not all of these components are required for every embodiment of the device 900, and there may be more than one of any given components in various embodiments of the device 900.

The device 900 may include one or more processors configured to execute computer program modules. The computer program modules may be configured to enable a user associated with the device 900 to interface with a system, (e.g., similar to the device 500) and/or external resources, and/or provide other functionality attributed herein to the device 900.

The device 900 may include the electronic storage 940, one or more processors 920, and/or other components. The device 900 may include communication lines, or ports to enable the exchange of information with a network and/or other computing platforms (e.g., the network interface 970). Illustration of the device 900 in FIG. 9 is not intended to be limiting. The device 900 may include a plurality of hardware, software, and/or firmware components operating together to provide the functionality attributed herein to the device 900. For example, the device 900 may be implemented by a cloud of computing platforms operating together as the device 900.

The electronic storage 940 (herein referred to collectively as the electronic storages 940 or individually as the electronic storage 940) may be directly or indirectly in operative electronic communication with the processor 920 may comprise non-transitory storage media that electronically stores information. The electronic storage media of the electronic storage 940 may include one or both of system storage that is provided integrally (i.e., substantially non-removable) with the device 900 and/or removable storage that is removably connectable to the device 900 via, for example, a port (e.g., a USB port, an IEEE 1394 port, a THUNDERBOLT™ port, etc.) or a drive (e.g., a disk drive, flash drive, or solid-state drive etc.). The electronic storage 940 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash memory, etc.), and/or other electronically readable storage media. The electronic storage 940 may include one or more virtual storage resources (e.g., cloud storage, a virtual private network, and/or other virtual storage resources). The electronic storage 940 may store software algorithms, information determined by the processor 920, information received from the device 900, information received from the system or another remote platform, and/or other information that enables the device 900 to function as described herein.

The processor 920 (herein referred to collectively as the processors 920 or individually as the processor 920) may be configured to provide information processing capabilities in the device 900. As such, the processor 920 may include one or more of a digital processor, an analog processor, a digital circuit designed to process information, an analog circuit designed to process information, a state machine, and/or other mechanisms for electronically processing information. Although the processor 920 is shown in FIG. 9 as a single entity, this is for illustrative purposes only. In some embodiments, the processor 920 may include a plurality of processing units. These processing units may be physically located within the same device, or the processor 920 may represent processing functionality of a plurality of devices operating in coordination. The processor 920 may be configured to execute one or more of the modules disclosed herein, and/or other modules. The processor 920 may be configured to execute one or more of the modules disclosed herein, and/or other modules by software; hardware; firmware; some combination of software, hardware, and/or firmware; and/or other mechanisms for configuring processing capabilities on the processor 920. As used herein, the term "module" may refer to any component or set of components that perform the functionality attributed to the module. This may include one or more physical processors during execution of processor readable instructions, the processor readable instructions, circuitry, hardware, storage media, or any other components. Various modules or portions thereof may be implemented in any of various ways, including procedure-based techniques, component-based techniques, and/or object-oriented techniques, among others. For example, the program instructions may be implemented using ActiveX controls, model-view-controller (MVC) principles, application programming interfaces (APIs), system-specific programming languages and principles, cross-platform programming languages and principles, pre-compiled programming languages, "bytecode" programming languages, object-oriented programming principles or languages, other programming principles or languages, JavaBeans, Microsoft Foundation Classes (MFC), Streaming SIMD Extension (SSE), or other technologies or methodologies, as desired.

It should be appreciated that although the modules disclosed herein are illustrated in FIG. 9 as being implemented within a single processing unit, in embodiments in which the processor 920 includes multiple processing units, one or more of modules disclosed herein may be implemented remotely from the other modules. The description of the functionality provided by the different modules disclosed herein is for illustrative purposes, and is not intended to be limiting, as any of modules described herein may provide more or less functionality than is described. For example, one or more of modules disclosed herein may be eliminated, and some or all of its functionality may be provided by other ones of modules disclosed herein. As another example, the processor 920 may be configured to execute one or more additional modules that may perform some or all of the functionality attributed herein to one of modules disclosed herein.

The device 900 may be configured by machine-readable instructions. Such machine-readable instructions may include one or more instruction modules. The instruction modules may include computer program modules, which may be similar to, for example, at least a portion of the methods described herein. The instruction modules may include one or more of the modules and methods disclosed herein and/or other instruction modules and methods.

The network interface 970 (herein referred to collectively as the network interfaces 970 or individually as the network interface 970) may be directly or indirectly in operative electronic communication with, inter alia, the processor 920. The network interface 970 may operatively link the processor 920 and/or the device 900 with one or more other computing platforms, remote platforms, and/or external resources via one or more electronic communication links. For example, such electronic communication links may be established, at least in part, via a network such as the internet and/or other networks using, for example, TCP/IP or cellular hardware enabling wired or wireless (e.g., cellular, 2G, 3G, 4G, 4G LTE, 5G, or WIFI®) communication. It will be appreciated that this is not intended to be limiting, and that the scope of this disclosure includes embodiments in which the device 900, one or more other computing platforms, remote platforms, and/or external resources may be operatively linked via some other communication media.

The processor 920 may be directly or indirectly in operative electronic communication with one or more displays 916 (herein referred to collectively as the electronic storages 940 or individually as the electronic storage 940). The display 916 may include a device (or "hardware component") that displays "display data" to form an image or images, such as, but not limited to, a picture, text, a desktop background, a gaming background, a video, an application window etc. One example of the display 916 may include an integrated display as found in electronic devices such as handheld computing devices, electronic book readers, mobile telephones (smartphones), personal-digital-assistants (PDAs), wearable devices (smart-watches, smart-glasses, etc.). The display 916 may employ any appropriate display technology, such as for example, LCD flat panel, LED flat panel, flexible panels, etc., and may include other display hardware that may, as needed for a particular electronic device, be operatively coupled to other devices and components. Therefore, the display 916 may include display hardware such as, but not limited to, a frame buffer, hardware display drivers, etc. that store and refresh display data to be displayed by the display 916. Also, the display 916 may include integrated hardware for implementation of touchscreen functionality such that the display is operative to receive user input by touch or via a stylus.

The display 916 may be configurable for indicating various readings, settings, interfaces, and alerts for the user. In some implementations, the display 916 may display a touchscreen-interactive application.

Figure 10:
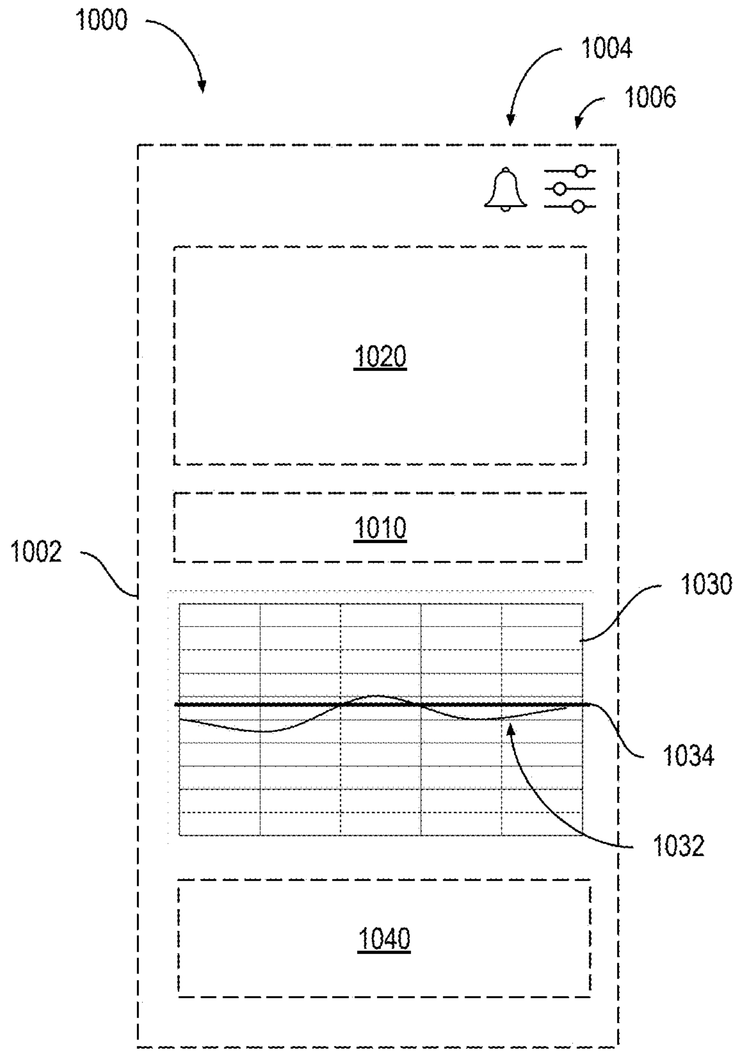
FIG. 10 illustrates a display presenting an example display interface, according to an embodiment.

FIG. 10 illustrates a display 1000 presenting an example display interface 1002, according to an embodiment. The display interface 1002 may be displayed on a display similar to, for example the display 916 Accordingly, it will be understood that the particular presentation or arrangement shown in on the display interface 1002 is not a limitation on the present disclosure. For example, various embodiments may be incorporated into different displays without departing from the present disclosure.

An interface module 1004 may indicate a presence and/or quantity of notifications for a user. The interface module 1004 may be configured for prominence, and the interface module 1004 may also be configured to be hidden if there is not an alert to communicate to a user of the device. The interface module 1004 may be selectable such that, when selected, display of the interface module 1020 may be toggled.

An interface module 1006 may include a selectable icon configured to toggle access to configuration settings of the application and/or an ambient sensing device. When such settings are updated, they may be pushed, for example over-the-air (OTA) to the ambient sensing device for local storage thereon.

An interface module 1010 may indicate current and/or historical readings or thresholds from the ambient sensing device related to ambient sensors onboard the ambient sensing device and/or remote probe sensors connected to the ambient sensing device.

An interface module 1020 may include a notifications area. The notifications area may indicate historical and/or current data regarding readings received from an ambient sensing device, and the notifications area may include historical and/or current alerts received from the ambient sensing device.

An interface module 1030 may include a plot 1032 of a measured property with a threshold 1034. The plot 1032 may include a scatter, line, or other plot of a property on a vertical axis against time on the horizontal axis, over a selected range of time. The threshold 1034 may represent the current setting of an alert threshold for the property (e.g., temperature, humidity, light, acceleration, etc.) indicated on the plot 1032.

In some implementations, a user may interact with a touchscreen of a mobile device (e.g., a capacitive touchscreen) using gestures (e.g., sliding with 1 or more finger-point-of-contact, pinching, etc.) to manipulate the ranges of the axes of the plot 1032 and/or the threshold 1034.

An interface module 1040 may include a table displaying, for example, status data (e.g., connection status data, power supply status data, etc.), historical sensor readings data, and/or threshold settings.

The following figures illustrate example methods and operations thereof. In some implementations, a method illustrated herein may include additional operations, fewer operations, differently arranged operations, or different operations than the operations depicted in the following figures. Moreover, or in the alternative, two or more of the operations depicted in the following figures may be performed at least partially in parallel.

In implementations of the methods illustrated in the following figures, various operations may be performed by one or more hardware processors configured by machine-readable instructions (e.g., instructions stored electronically on an electronic storage medium), which may include a module in accordance with one or more embodiments. Such a hardware processor may include one or more processing devices (e.g., one or more digital processors, analog processors, digital circuits designed to process information, analog circuits designed to process information, state machines, and/or other mechanisms for electronically processing information). The one or more processing devices may include one or more devices configured through hardware, firmware, and/or software, which may be specifically designed for execution of one or more of the operations of methods illustrated herein.

Figure 11:
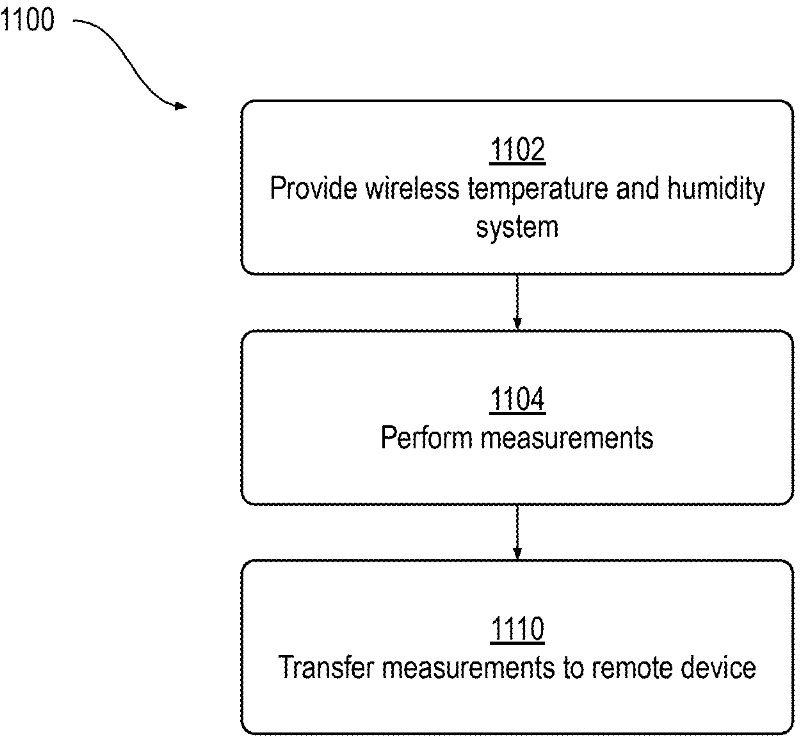
FIG. 11 is a flowchart illustrating an example method, according to one or more implementations herein.

FIG. 11 is a flowchart illustrating an example method 1100, according to one or more implementations herein. In some implementations, one or more operations illustrated in FIG. 11 may be performed by one or more of the devices, components, operations, or aspects depicted in FIG. 1 through FIG. 10, in concert, in the alternative, or in combinations thereof. In some implementations, one or more operations may be performed by another device, system, or group of devices or systems separate from or including these. Additionally, or alternatively other devices, components, or systems, may be employed to perform the operations.

An operation 1102 may include providing a temperature and humidity monitoring system and may be performed alone or in combination with one or more other operations depicted in FIG. 11. The temperature and humidity monitoring system may include for example an ambient sensing device similar to the ambient sensing device 110, and a remote probe similar to the remote probe 122.

An operation 1104 may include performing measurements by the temperature and humidity monitoring system and may be performed alone or in combination with one or more other operations depicted in FIG. 11. Measurements may include, for example, a container media temperature, an ambient temperature, an ambient humidity, an ambient luminance, and/or an acceleration.

An operation 1110 may include transferring the measurements from the temperature and humidity monitoring system to a remote device and may be performed alone or in combination with one or more other operations depicted in FIG. 11. The transfer of the measurements (as readings/data) may take place over a wired or wireless connection between the temperature and humidity monitoring system and a remote device.

Figure 12:
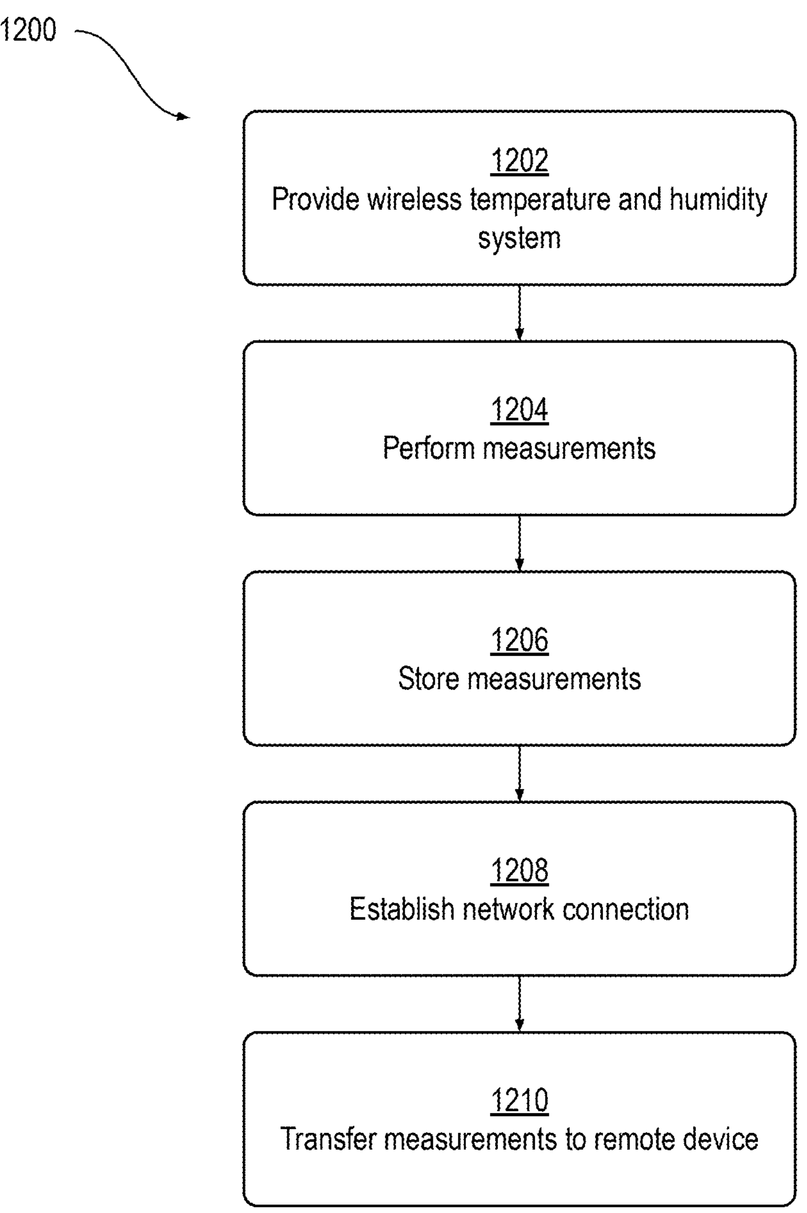
FIG. 12 is a flowchart illustrating an example method, according to one or more implementations herein.

FIG. 12 is a flowchart illustrating an example method 1200, according to one or more implementations herein. In some implementations, one or more operations illustrated in FIG. 12 may be performed by one or more of the devices, components, operations, or aspects depicted in FIG. 1 through FIG. 10, in concert, in the alternative, or in combinations thereof. In some implementations, one or more operations may be performed by another device, system, or group of devices or systems separate from or including these. Additionally, or alternatively other devices, components, or systems, may be employed to perform the operations.

An operation 1202 may include providing a temperature and humidity monitoring system and may be performed alone or in combination with one or more other operations depicted in FIG. 12. The operation 1202 may be, for example, similar to the operation 1102.

An operation 1204 may include performing measurements by the temperature and humidity monitoring system and may be performed alone or in combination with one or more other operations depicted in FIG. 12. The operation 1204 may be, for example, similar to the operation 1104.

An operation 1206 may include storing the measurements internally to the temperature and humidity monitoring system and may be performed alone or in combination with one or more other operations depicted in FIG. 12. The measurements may be stored as data onboard an ambient sensing device of the temperature and humidity monitoring system.

An operation 1208 may include establishing a network connection and may be performed alone or in combination with one or more other operations depicted in FIG. 12. In some instances, the operation 1208 may be performed after a lost network connection, at an interval, or during a wake activity.

An operation 1210 may include transferring the measurements from the temperature and humidity monitoring system to a remote device and may be performed alone or in combination with one or more other operations depicted in FIG. 12. The operation 1210 may be, for example, similar to the operation 1110.

Figure 13:
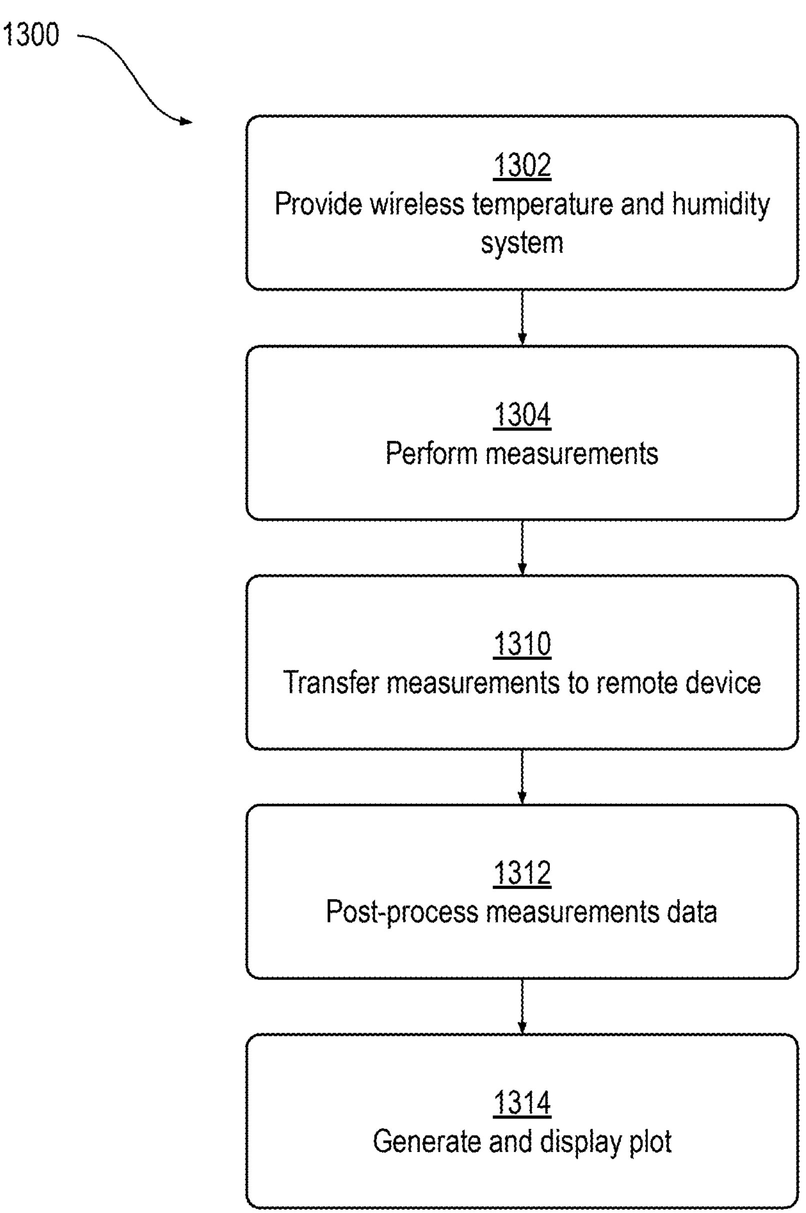
FIG. 13 is a flowchart illustrating an example method, according to one or more implementations herein.

FIG. 13 is a flowchart illustrating an example method 1300, according to one or more implementations herein. In some implementations, one or more operations illustrated in FIG. 13 may be performed by one or more of the devices, components, operations, or aspects depicted in FIG. 1 through FIG. 10, in concert, in the alternative, or in combinations thereof. In some implementations, one or more operations may be performed by another device, system, or group of devices or systems separate from or including these. Additionally, or alternatively other devices, components, or systems, may be employed to perform the operations.

An operation 1302 may include providing a temperature and humidity monitoring system and may be performed alone or in combination with one or more other operations depicted in FIG. 13. The operation 1302 may be, for example, similar to the operation 1102 or the operation 1202.

An operation 1304 may include performing measurements by the temperature and humidity monitoring system and may be performed alone or in combination with one or more other operations depicted in FIG. 13. The operation 1304 may be, for example, similar to the operation 1104 or the operation 1204.

An operation 1310 may include transferring the measurements from the temperature and humidity monitoring system to a remote device and may be performed alone or in combination with one or more other operations depicted in FIG. 13. The operation 1310 may be, for example, similar to the operation 1110 or the operation 1210. It will be understood that the operation 1310 may occur in a different order than depicted in FIG. 13 in different implementations.

An operation 1312 may include post-processing the measurements data and may be performed alone or in combination with one or more other operations depicted in FIG. 13. The post-processing of the measurements data may include, for example, normalization, calibration, smoothing, digitization, tabulating, creating alerts, etc.

An operation 1314 may include generating and displaying a plot and may be performed alone or in combination with one or more other operations depicted in FIG. 13.

The invention is limited only by the appended claims. Variations, characteristics, advantages, implementations, constructions, arrangements, terminology, materials, dimensions, embodiments, illustrations, depictions, and examples composing the above description and accompanying drawings show some possible implementations of the invention without limiting the invention. It is not necessary that every implementation of the invention achieve or possess every advantage, purpose, or characteristic identified herein, and as such, one skilled in the art may effect various additions, changes, modifications, or omissions without departing from the scope or spirit of the invention or its legal equivalents.

All ranges are inclusive of the stated limits, the orders of magnitude thereof, and all values and ranges substantially therebetween unless otherwise defined. Unless otherwise stated, every use of "and" forms an inclusive list comprising at least the conjoined elements, and every use of "or" forms an inclusive list comprising at least one element of conjoined elements. Unless otherwise stated, singular usage (e.g., 'a', 'an', or 'the') includes plurals of the same.

The order of recitations in a claim do not imply a temporal or ordered relationship unless unavoidable by the plain language of that claim. No claim may be interpreted to invoke 35 U.S.C. § 112(f) unless that claim recites "means for" or "step for."

We claim:

1. An ambient sensing device, comprising:

an ambient temperature sensor;

an ambient humidity sensor;

an accelerometer;

a light sensor;

a processor in electronic communication with the ambient temperature sensor, the ambient humidity sensor, the accelerometer, and the light sensor;

an electronic storage unit comprising non-volatile memory in electronic communication with the processor;

a networking device in electronic communication with the processor and configured to transmit data to a remote device via a wireless network connection; and a data port in electronic communication with the processor;

wherein the processor is configured to:

determine whether a remote probe including a remote probe sensor has been installed to the data port;

store the data on the electronic storage unit including an ambient temperature measurement measured by the ambient temperature sensor, an ambient humidity measurement measured by the ambient humidity sensor, an accelerometer measurement measured by the accelerometer, and a light measurement measured by the light sensor, and, if the remote probe sensor has been installed to the data port, a remote probe measurement measured by the remote probe sensor;

after the wireless network connection is established, retrieve the data stored on the electronic storage unit and instruct the networking device to transmit the data to the remote device; and instruct the networking device to transmit an alert to the remote device, wherein the alert is sent following a triggering of an event determined by an event parameter.

2. The ambient sensing device of claim 1, wherein the remote probe sensor includes a remote temperature sensor and the remote probe includes fitting configured to secure the remote probe to a container such that the remote temperature sensor is disposed within the container in thermal communication with a fluid disposed within the container.

3. An ambient sensing device, comprising:

an ambient temperature sensor;

an ambient humidity sensor;

a processor in electronic communication with the ambient temperature sensor and the ambient humidity sensor;

a networking device in electronic communication with the processor and configured to transmit data to a remote device via a network connection; and a data port in electronic communication with the processor;

wherein the processor is configured to:

determine whether a remote probe including a remote probe sensor has been installed to the data port; and after the network connection is established, instruct the networking device to transmit the data to the remote device, wherein the data includes one or more of an ambient temperature measurement measured by the ambient temperature sensor, an ambient humidity measurement measured by the ambient humidity sensor, or, if the remote probe sensor has been installed to the data port, a remote probe measurement measured by the remote probe sensor.

4. The ambient sensing device of claim 3, wherein the processor is configured to instruct the networking device to transmit an alert to the remote device.

5. The ambient sensing device of claim 4, wherein the alert is sent following a triggering of an event determined by an event parameter.

6. The ambient sensing device of claim 3, wherein the remote probe sensor includes a remote temperature sensor and the remote probe includes fitting configured to secure the remote probe to a container such that the remote temperature sensor is disposed within the container in thermal communication with a fluid disposed within the container.

7. The ambient sensing device of claim 3, wherein the data includes an ambient temperature measurement measured by the ambient temperature sensor, an ambient humidity measurement measured by the ambient humidity sensor, and, if a probe sensor has been installed to the data port, a remote probe measurement measured by the remote probe sensor.

8. The ambient sensing device of claim 3, wherein the ambient sensing device includes an electronic storage unit in electronic communication with the processor and the processor is configured to store the data on the electronic storage unit.

9. The ambient sensing device of claim 8, wherein the processor is configured to, after the network connection is established, retrieve the data stored on the electronic storage unit for transmission via the networking device.

10. The ambient sensing device of claim 8, wherein the processor is configured to:

receive a transmission schedule from the remote device;

store the transmission schedule on the electronic storage unit; and transmit the data via the networking device to the remote device according to the transmission schedule.

11. The ambient sensing device of claim 10, wherein the transmission schedule is a function of an event parameter.

12. The ambient sensing device of claim 3, wherein the data includes an alert.

13. The ambient sensing device of claim 3, wherein the ambient sensing device further includes an accelerometer in electronic communication with the processor and a light sensor in electronic communication with the processor.

14. The ambient sensing device of claim 13, wherein the data includes:

the ambient temperature measurement measured by the ambient temperature sensor;

the remote probe measurement measured by the remote probe sensor;

the ambient humidity measurement measured by the ambient humidity sensor; and a light measurement measured by the light sensor.

15. The ambient sensing device of claim 3, further comprising an electrical port configured to receive an electrical plug configured for delivery of electrical power from an external electrical power source, wherein the processor is further configured to, in response to a detected loss of electrical power at the electrical port, switch a power supply to the ambient sensing device from the external electrical power source to an internal electrical power source of the ambient sensing device.

16. The ambient sensing device of claim 15, wherein the processor is further configured to, upon switching the power supply to the ambient sensing device, instruct the networking device to transmit a power status alert to the remote device.

17. The ambient sensing device of claim 3, wherein the network connection is a wireless network connection.

18. The ambient sensing device of claim 17, wherein the wireless network connection is a cellular network connection or a local area network connection.

19. The ambient sensing device of claim 3, wherein the processor is configured to select one of a cellular network connection or a local area network connection as the network connection based on one or more of a signal strength comparison or user input.

20. The ambient sensing device of claim 3, wherein the ambient sensing device includes a display in electronic communication with the processor, and the display is configured to display the data.

21. A method for monitoring temperature and humidity, comprising:

providing an ambient sensing device, comprising:

an ambient temperature sensor;

an ambient humidity sensor;

an accelerometer;

a light sensor;

a processor in electronic communication with the ambient temperature sensor, the ambient humidity sensor, the accelerometer, and the light sensor;

an electronic storage unit comprising non-volatile memory in electronic communication with the processor;

a networking device in electronic communication with the processor and configured to transmit data to a remote device via a wireless network connection; and a data port in electronic communication with the processor;

determining, by the processor, whether a remote probe including a remote probe sensor has been installed to the data port;

storing, by the processor, the data on the electronic storage unit including an ambient temperature measurement measured by the ambient temperature sensor, an ambient humidity measurement measured by the ambient humidity sensor, an accelerometer measurement measured by the accelerometer, and a light measurement measured by the light sensor, and, if the remote probe sensor has been installed to the data port, a remote probe measurement measured by the remote probe sensor; and after the wireless network connection is established, retrieving, by the processor, the data stored on the electronic storage unit and instruct the networking device to transmit the data to the remote device.

* * * * *